US011319534B2

(12) United States Patent
Steemers et al.

(10) Patent No.: US 11,319,534 B2
(45) Date of Patent: May 3, 2022

(54) METHODS AND COMPOSITIONS FOR NUCLEIC ACID SEQUENCING

(71) Applicant: ILLUMINA, INC., San Diego, CA (US)

(72) Inventors: Frank J. Steemers, Encinitas, CA (US); Sasan Amini, Redwood City, CA (US); Kevin L. Gunderson, Encinitas, CA (US); Natasha Pignatelli, Berkeley, CA (US); Igor Goryshin, Madison, WI (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/735,348

(22) Filed: Jan. 6, 2020

(65) Prior Publication Data

US 2020/0157530 A1    May 21, 2020

Related U.S. Application Data

(63) Continuation of application No. 14/766,089, filed as application No. PCT/US2013/031023 on Mar. 13, 2013, now Pat. No. 10,557,133.

(51) Int. Cl.
*C12N 15/10* (2006.01)
*C12Q 1/6806* (2018.01)
*C12Q 1/6869* (2018.01)

(52) U.S. Cl.
CPC ....... *C12N 15/1065* (2013.01); *C12Q 1/6806* (2013.01); *C12Q 1/6869* (2013.01)

(58) Field of Classification Search
CPC . C12N 15/1065; C12Q 1/6806; C12Q 1/6869
See application file for complete search history.

(56) References Cited

U.S. PATENT DOCUMENTS

| 5,130,238 A | 7/1992 | Malek et al. |
|---|---|---|
| 5,185,243 A | 2/1993 | Ullman et al. |
| 5,223,414 A | 6/1993 | Zarling et al. |
| 5,455,166 A | 10/1995 | Walker |
| 5,573,907 A | 11/1996 | Carrino et al. |
| 5,599,675 A | 2/1997 | Brenner |
| 5,641,658 A | 6/1997 | Adams et al. |
| 5,679,524 A | 10/1997 | Nikiforov et al. |
| 5,750,341 A | 5/1998 | Macevicz |
| 5,858,671 A | 1/1999 | Jones |
| 5,965,443 A | 10/1999 | Reznikoff et al. |
| 6,210,891 B1 | 4/2001 | Nyren et al. |
| 6,214,587 B1 | 4/2001 | Dattagupta et al. |
| 6,258,568 B1 | 7/2001 | Nyren |
| 6,274,320 B1 | 8/2001 | Rothberg et al. |
| 6,355,431 B1 | 3/2002 | Chee et al. |
| 6,437,109 B1 | 8/2002 | Reznikoff et al. |
| 6,593,113 B1 | 7/2003 | Tenkanen et al. |
| 6,777,187 B2 | 8/2004 | Makarov et al. |
| 6,828,098 B2 | 12/2004 | Langmore et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,138,267 B1 | 11/2006 | Jendrisak et al. |
| 7,211,414 B2 | 5/2007 | Hardin et al. |
| 7,244,559 B2 | 7/2007 | Rothberg et al. |
| 7,315,019 B2 | 1/2008 | Turner |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,537,897 B2 | 5/2009 | Brenner et al. |
| 7,582,420 B2 | 9/2009 | Oliphant et al. |
| 7,595,883 B1 | 9/2009 | El Gamal et al. |
| 7,611,869 B2 | 11/2009 | Fan |
| 7,670,810 B2 | 3/2010 | Gunderson et al. |
| 7,696,340 B2 | 4/2010 | Goldman et al. |
| 7,741,463 B2 | 6/2010 | Gormley et al. |
| 8,003,354 B2 | 8/2011 | Shen et al. |
| 8,383,345 B2 | 2/2013 | Shendure et al. |
| 8,563,477 B2 | 10/2013 | Smith et al. |
| 8,829,171 B2 | 9/2014 | Steemers et al. |
| 9,074,251 B2 | 7/2015 | Steemers et al. |
| 9,644,198 B2 | 5/2017 | Walder et al. |
| 9,644,199 B2 | 5/2017 | Belyaev |
| 2001/0046669 A1 | 11/2001 | McCobie et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2004/0110191 A1 | 6/2004 | Winkler et al. |
| 2004/0259229 A1 | 12/2004 | Thevelein et al. |

(Continued)

FOREIGN PATENT DOCUMENTS

| EP | 0320308 | 11/1993 |
|---|---|---|
| EP | 0336731 | 5/1994 |

(Continued)

OTHER PUBLICATIONS

Twining et al. (Journal of Biological Chemistry 276.25 (2001): 23135-23143.). (Year: 2001).*
Amini, Sasan et al., "Haplotype-resolved whole-genome sequencing by contiguity-preserving transposition and combinatorial indexing", Nature Genetics, vol. 46 No. 12, Dec. 2014, 1343-1349.
Amini, Sasan et al., "Supplementary information for: Haplotype-resolved whole-genomes sequencing by contiguity-preserving transposition and combinatorial indexing", Nature Genetics, vol. 46 No. 12, Dec. 2014, 1-16.
Australian Patent Examination Report No. 1 dated Aug. 2, 2016— Australian Patent Application No. 2012212148.
Australian Examination report No. 2 for standard patent application dated May 24, 2017 for Australian Patent Application No. 2012212148.
Bains, et al., "A novel method for nucleic acid sequence determination", J. Theor Biol., 135(3), 1988, 303-307.
Boeke et al., "Transcription and Reverse Transcriptiion of Retrotransposons," Annu. Rev. Microbiol. 1989. 43:403-34.

(Continued)

*Primary Examiner* — Sahana S Kaup
(74) *Attorney, Agent, or Firm* — Fletcher Yoder, P.C.

(57) ABSTRACT

Embodiments of the present invention relate to sequencing nucleic acids. In particular, embodiments of the methods and compositions provided herein relate to preparing nucleic acid templates and obtaining sequence data therefrom.

24 Claims, 16 Drawing Sheets

(56) References Cited

U.S. PATENT DOCUMENTS

| | | |
|---|---|---|
| 2005/0191698 A1 | 9/2005 | Chee et al. |
| 2006/0024681 A1 | 2/2006 | Smith et al. |
| 2006/0040297 A1 | 2/2006 | Leamon et al. |
| 2006/0177833 A1* | 8/2006 | Brenner ............. C12N 15/1093 435/6.12 |
| 2006/0216309 A1 | 9/2006 | Holden |
| 2006/0236413 A1 | 10/2006 | Ivics et al. |
| 2006/0257905 A1 | 11/2006 | Freije et al. |
| 2006/0292611 A1 | 12/2006 | Berka et al. |
| 2007/0128610 A1 | 6/2007 | Buzby |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2008/0234136 A1 | 9/2008 | Drmanac et al. |
| 2008/0242560 A1 | 10/2008 | Gunderson et al. |
| 2009/0026082 A1 | 1/2009 | Rothberg et al. |
| 2009/0032401 A1 | 2/2009 | Ronaghi et al. |
| 2009/0047680 A1 | 2/2009 | Lok |
| 2009/0088331 A1 | 4/2009 | Wu et al. |
| 2009/0127589 A1 | 5/2009 | Rothberg et al. |
| 2009/0176234 A1 | 7/2009 | Drmanac et al. |
| 2010/0022403 A1 | 1/2010 | Kurn et al. |
| 2010/0069263 A1 | 3/2010 | Shendure et al. |
| 2010/0111768 A1 | 5/2010 | Banerjee et al. |
| 2010/0120098 A1* | 5/2010 | Grunenwald ......... C12Q 1/6855 435/91.2 |
| 2010/0137143 A1 | 6/2010 | Rothberg et al. |
| 2010/0282617 A1 | 11/2010 | Rothberg et al. |
| 2011/0014657 A1 | 1/2011 | Rigatti et al. |
| 2011/0059865 A1 | 3/2011 | Smith et al. |
| 2011/0124518 A1 | 5/2011 | Cantor |
| 2011/0311506 A1 | 12/2011 | Craig |
| 2012/0053063 A1 | 3/2012 | Rigatti et al. |
| 2012/0129704 A1 | 5/2012 | Gunderson et al. |
| 2012/0208705 A1 | 8/2012 | Steemers et al. |
| 2012/0208724 A1 | 8/2012 | Steemers et al. |
| 2012/0270305 A1 | 10/2012 | Reed et al. |
| 2012/0283108 A1* | 11/2012 | Sampas ................ C12Q 1/6883 506/2 |
| 2012/0316074 A1* | 12/2012 | Saxonov ................ C12N 15/10 506/2 |
| 2013/0017978 A1 | 1/2013 | Kavanagh et al. |
| 2013/0203605 A1 | 8/2013 | Shendure et al. |
| 2013/0338042 A1 | 12/2013 | Shen et al. |
| 2014/0079923 A1 | 3/2014 | George et al. |
| 2014/0093916 A1 | 4/2014 | Belyaev |
| 2014/0194324 A1 | 7/2014 | Gormley et al. |
| 2014/0235506 A1 | 8/2014 | Hindson et al. |
| 2019/0040382 A1 | 2/2019 | Steemers et al. |

FOREIGN PATENT DOCUMENTS

| | | |
|---|---|---|
| EP | 0439182 | 4/1996 |
| EP | 2635679 | 9/2013 |
| EP | 2670894 | 12/2013 |
| EP | 2712931 | 4/2014 |
| JP | 2012506704 | 3/2012 |
| JP | 2013150611 A | 8/2013 |
| JP | 2013535986 A | 9/2013 |
| RU | 2252964 C2 | 5/2005 |
| WO | WO1989/09835 | 10/1989 |
| WO | WO1989/10977 | 11/1989 |
| WO | WO1989/12696 | 12/1989 |
| WO | WO1990/01069 | 2/1990 |
| WO | WO1991/006678 | 5/1991 |
| WO | WO1995/023875 | 9/1995 |
| WO | WO1998044151 | 10/1998 |
| WO | WO2004/018497 | 3/2004 |
| WO | WO2004042078 | 5/2004 |
| WO | WO2005/065814 | 7/2005 |
| WO | WO2005100585 | 10/2005 |
| WO | WO2006/047183 | 5/2006 |
| WO | WO2007098279 | 8/2007 |
| WO | WO2007/123744 | 11/2007 |
| WO | WO2010002883 | 1/2010 |
| WO | WO2010048605 | 4/2010 |
| WO | WO2011106314 | 9/2011 |
| WO | WO2012/025250 | 3/2012 |
| WO | 2012048341 A1 | 4/2012 |
| WO | WO2012/058096 | 5/2012 |
| WO | WO2012061832 | 5/2012 |
| WO | WO-2012061832 A1 * | 5/2012 ......... C12N 15/1093 |
| WO | WO2012/108864 | 8/2012 |
| WO | WO2012103545 | 8/2012 |
| WO | WO2012106546 | 8/2012 |
| WO | WO-2012106546 A2 * | 8/2012 ......... C12N 15/1093 |
| WO | WO2013131962 | 9/2013 |
| WO | WO2013/177220 | 11/2013 |
| WO | WO2013/184796 | 12/2013 |
| WO | WO2014/108810 | 7/2014 |
| WO | 2014136930 A1 | 9/2014 |
| WO | WO2014/142850 | 9/2014 |
| WO | 2015031691 A1 | 3/2015 |
| WO | 2015103339 A1 | 7/2015 |

OTHER PUBLICATIONS

Brown, et al., "Retroviral Integration: Structure of the Initial Covalent Product and Its Precursor, and a Role for the Viral IN Protein", PNAS, 86, 1989, 2525-9.

Canadian Examination Report dated Mar. 21, 2017 in Canadian Patent Application No. 2,826,121.

Chinese Office Action, Application No. CN201280012945.4 withEnglish Translations, State Intellectual Property Office, PRC China, dated Nov. 6, 2015, 21 pages.

Cockroft, et al., "A single-molecule nanopore device detects DNA polymerase activity with single-nucleotide resolution", J. Am. Chem. Soc, 130(3), 2008, 818-820.

Colegio, et al., "In vitro transposition system for efficient generation of random mutants of Campylobacter jejuni", J. Bacteriol, 183, 2001, 2384-8.

Craig, "V(D)J Recombination and Transposition: Closer Than Expected", Science, 271, Mar. 1996, p. 1512.

Craig, "Transposon Tn7", Review in: Curr Top Microbiol Immunol, 204, 1996, 27-48.

Deamer, et al., "Characterization of nucleic acids by nanopore analysis", ACC Chem Res, 35(10), 2002, 817-825.

Deamer, et al., "Nanopores and nucleic acids: prospects for ultrarapid sequencing", Trends Biotechnol, 18(4), 2000, 147-151.

Dean, et al., "Comprehensive human genome amplification using multiple displacement amplification", PNAS, 99, 2002, 5261-5266.

Drmanac, et al., "Accurate sequencing by hybridization for DNA diagnostics and individual genomics", Nature Biotechnology, 16(1), 1998, 54-8.

Duitama et al., "ReFHap: A Reliable and Fast Algorithm for Single Individual Haplotyping," 2010 https://dna.engr.uconn.edu/bibtexmngr/upload/Dal.10.pdf.

Duitama, et al., Proceedings of the First ACM International Conference on Bioinformatics and Computational Biology, 160-169, 2010.

EPO Communication pursuant to Article 94(3) EPC in 12741945.5, dated Oct. 26, 2015.

EPO Extended Search Report dated Sep. 22, 2014 in Application No. 12741945.5-1406/2670894.

EPO Communication pursuant to Article 94(3) EPC in 12741945.5 dated Jul. 7, 2016.

EPO, PCT Search Report and Written Opinion for PCT application No. PCT/US2014/070658, dated Jun. 23, 2015.

Ewing, et al., "Base-calling of automated sequencer traces using phred II Error probabilities", Genome Research, 8, 1998, 186-194.

Fodor, "Light-Directed, Spatially Addressable Parallel Chemical Synthesis", Science, vol. 251, 1991, 767-773.

Gloor, "Gene targeting in Drosophila", Methods Mol Biol. 260, 2004, 97-114.

Haapa, et al., "An efficient and accurate integration of mini-Mu transposons in vitro: a general methodology for functional genetic analysis and molecular biology applications", Nucleic Acids Research vol. 27, No. 13, 1999, 2777-2784.

(56) References Cited

OTHER PUBLICATIONS

Handelsman, J. et al., "Metagenomics: Application of Genomics to Uncultured Microorganisms", Microbiology and Molecular Biology Reviews, 68(4), Dec. 2004, 669-685.
Healy, Ken, "Nanopore-based single-molecule DNA analysis", Nanomed. 2(4), 2007, 459-481.
Ichikawa, et al., "In vitro transposition of transposon Tn3", J Biol Chem, 265, 1990, 18829-32.
International Search Report and Written Opinion, issued for PCT/US2015/056040, dated Jul. 11, 2016 (23 pages).
Joos, "Covalent attachment of hybridizable oligonucleotides to glass supports", Analytical Biochemistry, 247, 1997, 96-101.
JP OA w/English Translation for JP213-552641, Jan. 12, 2016, 7 pages.
Khandjian, "UV crosslinking of RNA to nylon membrane enhances hybridization signals", Mol. Bio. Rep, 11, 1986, 107-115.
Kirby, et al., "Cryptic plasmids of Mycobacterium avium Tn552 to the rescue", Molecular Microbiology, 43, 2002, 173-86.
Kleckner, et al., "Tn10 and IS10 transposition and chromosome rearrangements mechanism and regulation in vivo and in vitro", Curr Top Microbiol Immunol., 204, 1996, 49-82.
Korlach, et al., "Selective aluminum passivation for targeted immobilization of single DNA polymerase molecules in zero-mode waveguide nanosuuctures", PNAS, 105(4), 2008, 1176-1181.
Lage, Jose M. et al., "Whole genome analysis of genetic alterations in small DNA samples using hyperbranched strand displacement amplification and array—CGH", Genome Research, vol. 13, Issue 2, Feb., Feb. 2003, 294-307.
Lampe, et al., "A purified mariner transposase is sufficient to mediate transposition in vitro", EMBO J., 15, 1996, 5470-5479.
Levene, et al., "Zero-Mode Waveguides for Single-Molecule Analysis at high concentrations", Science 299, 2003, 682-686.
Li et al., "DNA molecules and configurations in a solid-state nanopore microscope", Nature Mater, 2(9), 2003, 611-615.
Lizardi, "Mutation detection and single-molecule counting using isothermal rolling-circle amplification", Nature Genetics, vol. 19, 1998, 225-232.
Lundquist et al., "Parallel confocal detection of single molecules in real time", Opt. Lett. 33(9), 2008, 1026-1028.
Mardis, E.R., "The impact of next-generation sequencing technology on genetics", Trends in Genetics 24, 2008, 133-141.
Mizuuchi, "In vitro transposition of bacteriophase Mu: abiochemical approach to a novel replication reaction", Cell, 35, 1983, 785-94.
Mizuuchi, Kiyoshi, "Transpositional Recombination: Mechanistic Insights from Studies of Mu and Other Elements", Annu. Rev. Biochem. 61, 1992, 1011-51.
Ohtsubo et al., "Bacterial insertion sequences", Curr. Top. Microbiol. Immunol. 204, 1996, 1-26.
Oroskar, et al., "Detection of immobilized amplicons by ELISA-like techniques", Clinical Chemistry 42, 1996, 1547-1555.
Parkinson et al., "Preparation of High Quality Next Generation Sequencing Libraries from Picogram Quantities of Target DNA," 2012 Genome Research.
Plasterk, "The Tc1/mariner transposon family", Curr Top Microbiol Immunol, 204, 1996, 125-43.
Reinhardt, J.A. et al., "De Novo Assembly Using Low-Coverage Short Read Sequence Data from the Rice Pathogen Pseudomonas Syringae pv. Oryzae", Genome Research 19(2), Feb. 2009, 294-305.
Rode et al., "New tools for integrated genetic and physical analyses of the *Escherichia coli* chromosome" Gene, 166 (1995) 1-9.
Ronaghi, M et al., "A Sequencing Method Based on Real-Time Phyrophosphate", Science. Jul. 17, 1998; 281 (5375):363-365 USE, Jul. 17, 1998, 363-365.
Ronaghi, M et al., "Real-time DNA sequencing using detection of pyrophosphate release", Anal. Biochem. Nov. 1, 1996; 242 (1):84-9, Nov. 1, 1996, 84-89.
Ronaghi, Mostafa , "Pyrosequencing sheds light on DNA sequencing", Genome Res, 11(1), 2001, 3-11.

Smith, et al., "Direct Mechanical Measurements of the Elasticity of Single DNA Molecules by Using Magnetic Beads", Science, 258, 1992, p. 1122.
Soni, et al., "Progress toward Ultrafast DNA Sequencing Using Solid-State Nanopores", Clin Chem, 53(11), 2007, 1996-2001.
Sorber, K. et al., "The Long March: A Sample Preparation Technique That Enhances Contig Length and Coverage by High-Throughput Short-Read Sequencing", PLoS ONE 2(10):e3495, Oct. 2008, 9 pages.
Strahl et al., "The language of covalent histone modifications,"Nature, vol. 403, pp. 41-45, Jan. 2000. (Year: 2000).
Taylor, et al., "Characterization of chemisorbed monolayers by surface potential measurements", J. Phys. D: Appl, Phys., 24, 1991, p. 1443.
Vincent, et al., "Helicase-dependent isothermal DNA amplification", EMBO Rep 5, Epub Jul. 9, 2004, 795-800.
Voordouw et al. "Studies on ColE1-plasmid DNA and its interactions with histones sedimentation velocity studies of monosidpserse complexes reconstituted with calfthymus histones. Nucleic Acids Research," vol. 4, No. 5, pp. 1207-1223, 1977. (Year 1977).
Walker, et al., "A Chemiluminescent DNA Probe Test Based on Strand Displacement Amplification", Molecular Methods for Virus Detection, 1995, Academic Press Inc. Ch 15, pp. 329-349., 1995.
Walker, et al., "Strand displacement amplification-an isothermal, in vitro DNA amplification technique", NAR, 20, 1992, 1691-1696.
Waterston et al., "More on the sequencing of the human genome," PNAS Mar. 18, 2003; vol. 100 No. 6 3022-3024.
Wilson, et al., "New transposon delivery plasmids for insertional mutagenesis in Bacillus anthracis", Journal of Microbiological Methods, 71, 2007, 332-335.
Wold, B. et al., "Sequence Census Methods for Functional Genomics", Nature Methods, 5(1), Jan. 2008, 19-21.
Zerbino D.R., et al., "Velvet: Algorithms for De Novo Short Read Assembly Using de Bruijn Graphs", Genome Research, 18(5), Mar. 2008, 821-829.
Zhang, et al., "A Novel Mechanism of Transposon-Mediated Gene Activation", PLoS Genetics el000689. Epub Oct. 16, 2009.
Communication under Rule 164(2)(a) EPC for Application No. 15 797 490.8 dated Jun. 21, 2018.
Parkinson, Nicholas J., et al. "Preparation of high-quality next-generation sequencing libraries from pictogram quantities of target DNA." Genome research 22.1 (2012): 125-133. (Year: 2012).
Filee et al., "Insertion Sequence Diversity in Archaea," Microbiology and Molecular Biology Reviews, vol. 71, No. I, pp. 121-157, Mar. 2007.
Ivics et al., "Targeted Sleeping Beauty Transposition in Human Cells", Molecular Therapy, vol. 15, No. 6, pp. 1137-1144, Jun. 2007.
Johnson et al., "DNA sequences at the ends of transposon Tn5 required for transposition," Nature, vol. 304, No. 5923, pp. 280-282, Jul. 1983.
Lehoux et al., "Defined Oligonucleotide Tag Pools and PCR Screening in Signature-Tagged Mutagenesis of Essential Genes from Bacteria," Biotechniques, vol. 26, No. 3, pp. 473-478,480, Mar. 1999.
Mahillon et al., "Insertion Sequences." Microbiology and Molecular Biology Reviews, vol. 62, No. 3, pp. 725-774, Sep. 1998.
Mardis, "The impact of next-generation sequencing technology on genetics," Annu Rev Genomics Hum Genet. 2008; 9:387-402.
Peck et al., "A method for high-throughput gene expression signature analysis," Genome biology 7.7 (2006): R61.
Raymond et al., "Targeted, haplotype-resolved resequencing of long segments of the human genome," Genomics 86 (2005) 759-766.
Seong et al., "Measurement of Enzyme Kinetics Using a Continuous-Flow Microfluidic System," Anal. Chem., 2003, 75 (13), pp. 3161-3167.
Simon et al., "Short-Read Sequencing Technologies for Transcriptional Analysis," Annual review of plant biology 60 (2009): 305-333.
The protocol for Roche 454 FLX Titanium ernPCR (2009).
Wong et al., ChiP'ing the mammalian genome: technical advances and insights into functional elements (Genome Med 1.89 (2009).

(56) References Cited

OTHER PUBLICATIONS

Wang, Haoyi, et al. "Calling Cards enable multiplexed identification of the genomic targets of DNA-binding proteins." Genome research 21.5 (2011): 748-755.
International Preliminary Report on Patentability in PCT application No. PCT/IB2014/000601, dated Jul. 14, 2015.
Adey, et al., "Ultra-low-input, tagmentation-based whole-genome bisulfite sequencing", vol. 22, No. 6, Mar. 30, 2012 (Mar. 30, 2012), XP055136909, ISN: 1088-9051, DOI: 10.1101/gr.136242.111, the whole document, 1139-1143.
Batzoglou, et al., "ARACHNE: a whole-genome shotgun assembler", Genome Research, 12(1), 2002, 177-189.
Chernoff, et al., "Molecular Analysis of the von Hippel-Lindau Disease Gene", Methods, Mol. Med. 53, 2001, 193-216.
Chinese Office Action in Application No. 201280012945.4 dated Apr. 17, 2015.
De Vries, et al., "PCR on Cell Lysates Obtained from Whole Blood Circumbents DNA Isoloation", Clin. Chem. 47, 2001, 1701-1702.
EPO communication pursuant to Article 94(c) EPC, dated Oct. 28, 2014, for Application No. 11802179.9.
GS FLX Titanium LV ernPCR Kit (Lib-L) protocol, Aug. 2008, 1-2. http://www.epibio.com/nextera.
International Search Report and Written Opinion for PCT/US12/23679, Applicant: University of Washington Through Its Center for Commercialization, dated Aug. 24, 2012.
International Search Report and The Written Opinion, issued for PCT/US2011/059642, dated Apr. 10, 2012, 12.
Office Action issued for U.S. Appl. No. 12/559,124 dated Mar. 27, 2012, 13 pages.
Supplementary European Search Report for Application EP12741945.5, Applicant University of Washington Through Its Center for Commercialization, dated Sep. 22, 2014.
Adey, "Rapid, low-input, low-bias construction of shotgun fragment libraries by high-density in vitro transposition", Genome Biology 11 r119, Dec. 8, 2010, 47 pages.
Adey, et al., "Rapid, low-input, low-bias construction of shotgun fragment libraries by high-density in vitro transposition", Genome Biology vol. 11 (12), 2010, R119.
Ball et al., "Targeted and genome-scale strategies reveal gene-body methylation signatures in human cells", Nat Biotechnol 27(4), 2009, 361-368.
Bansal et al., "An efficient and accurate algorithm for the haplotype assembly problem", Bioinformatics; 24(16), 2008, i153-9.
Ben Etti et al., "A mammalian microRNA cluster controls DNA methylation and telomere recombination via Rbl2-dependent regulation of DNA methyltransferases.", Nat Struct Mol Bioi 15(3), 2008, 268-279.
Benjamin, Bimber N. et al., "Whole-genome characterization of human and simian immunodeficiency virus intrahost diversity by ultra deep pyrosequencing", Journal of Virology, vol. 84, No. 22, Sep. 15, 2010, 12087-12092.
Bentley, et al., "Accurate whole human genome sequencing using reversible terminator chemistry", Nature, vol. 456, No. 7218, Nov. 6, 2008, 53-59.
Bimber, et al., "Whole-genome characterization of human and simian immunodeficiency virus intrahost diversity by uptradeep pyrosequencing", Journal of Virology, vol. 84, No. 22, 2010, 12087-12092.
Bloch, et al., "Purification of *Escherichia coli* chromosomal segements without cloning", Biochemical and Biophysical Research Communications, vol. 223, 1996, 104-111.
Branton, et al., "The potential and challenges of nanopore sequencing", Nature Biotechnology, vol. 26, No. 10, Oct. 2008, 1146-1153.
Braslavsky, et al., "Sequence information can be obtained from single DNA molecules", PNAS, 100(7), 2003, 3960-3964.
Brownlie, et al., "The Caenorhabditis briggsae genome contains active CbmaTl and Tcbl transposons", Molecular Genetics and Genomics, vol. 273, 2005, 92-101.
Caruccio, Nicholas et al., "Preparation of next-generation sequencing libraries using Nextera(TM) technology: simultaneous DNA fragmentation and adaptor tagging by in vitro transpoition". Methods in Molecular Biology, 733, Jan. 1, 2011, 241-255.
Chinese Office Action, "Application No. CN201280012945.4", dated May 28, 2014.
Clark, et al., "High sensitivity mapping of methylated cytosines", Nucleic Acids Research, vol. 22, No. 15, 1994, 2990-2997.
Cokus et al., "Shotgun bisulphite sequencing of the *Arabidopsis* genome reveals DNA methylation patterning", Nature 452,7184, 2008, 215-219.
Deng et al., "Targeted bisulfite sequencing reveals changes in DNA methylation associated with nuclear reprogramming.", Nat Biotechnol 27(4), 2009, 353-360.
Down et al., "A Bayesian deconvolution strategy for immunoprecipitation-based DNA methylome analysis.", Nat Biotechnol 26(7), 2008, 779-785.
Dressman, et al., "Transforming single DNA molecules into fluorescent magnetic particles for detection and enumeration of genetic variations", PNAS, 100(15), 2003, 8817-8822.
Drmanac, et al., "Human genome sequencing using unchained base reads on selfassembling DNA nanoarrays", Science.2009; 327(5961), 2009, 78-81.
Duan et al., "A three-dimensional model of the yeast genome", Nature; 465(7296), 2010, 363-7.
Eid, J et al., "Real-Time DNA Sequencing from Single Polymerase Molecules", Science 323, 2009, 133-138.
Fan et al., "Whole-genome molecular haplotyping of single cells.", Nat Biotech 29(1):, 2011,51-57.
Fraz, Syed et al., "Optimized library preparation method for next generation sequencing", Nature Methods, vol. 6, No. 10, Oct. 2009, 1-11.
Fullwood, Melissa J. et al., "Chromatin interaction analysis using paired-end tag sequencing", Current Protocols in Molecular Biology, Supplement 89, Jan. 21, 2010, 21.15.1-21.15.25.
Fullwood et al., "An oestrogen-receptor-bound human chromatin interactome", Nature 462, 2009, 58-64.
Gal, et al., "Direcctional cloning of native PCR products with preformed sticky ends Kautosticky PCR)", Molecular & General Genetics, vol. 260, No. 6, Jan. 1999, 569-573.
Geiss et al., "Direct multiplexed measurement of gene expression with colorcoded probe pairs", NatBiotechnol.; 26(3), 2008, 317-25.
Gnerre et al., "High-quality draft assemblies of mammalian genomes from massively parallel sequence data", Proc Natl Acad Sci USA., [Epub ahead of print] PubMedPMID: 21187386, Dec. 2, 20107.
Goodman, et al., "Identifying genetic determinants needed to establish a human gut symbiont in its habit", Cell Host & Microbe, vol. 6, Sep. 2009, 279-289.
Goryshin, et al., "Tn5 in Vitro Transposition*", vol. 273, No. 13, Issue of Mar. 27, 1998, 7367-7374.
Grunenwald, et al., "Rapid, high-throughput library preparation for next-generation sequencing, Nature Methods, Application Notes", Aug. 2010, iii-iv.
Grunenwald et al., "Nextera PCR-Free DNA Library Preparation for Next-Generation Sequencing", (Poster Presentation, AG8T)., 2011.
Gu et al., "Preparation of reduced representation bisulfite sequencing libraries for 'genome-scale DNA methylation profiling", NatProtoc 6(4), 2011, 468-481.
Haoyi, Wang et al., "Calling cards enable multiplexed identification of the genomic targets of DNA binding proteins", Genome Research, vol. 21, No. 5, May 2011, 748-755.
Harris, et al., "Comparison of sequencing-based methods to profile DNA methylation and identification of monoallelic epigenetic modifications.", Nat Biotechnol 28(10), 2010, 1097-1105.
Heredia, et al., "In vitro double transposition for DNA identification", Analytical Biochemistry 399, 2010, 78-83.
Hiatt et al., "Tag-directed assembly of locally derived short sequence reads", Nat Methods. 7(2), 2010, 119-22.
Jackson, et al., "Plasmid tagging for efficient large-scale sequence completion of entire clone inserts", BioTechniques, vol. 34, Mar. 2003, 604-608.
Johnson et al., "Genome-wide mapping of in vivo protein-DNA interactions", Science. 316(5830), 2007, 1497-502.

(56) References Cited

OTHER PUBLICATIONS

Keith, et al., "Algorithms for Sequence Analysis via Mutagenesis", Bioinformatics, vol. 20 No. 15; published online doi: 10.1093/bioinformatics/bth258, May 14, 2004, 2401-2410.
Keith, et al., "Unlocking Hidden Genomic Sequence", Nucleic Acids Research, vol. 32, No. 3, published online DOI: 10.1093/nar/gnh022, Feb. 18, 2004, e35.
Kidd et al., "Mapping and sequencing of structural variation from eight human genomes", Nature. 453 (7191), 2008, 56-64.
Kirby, J.R., "in vivo mutagenesis using EZ-Tn5ATM.", Methods in Enzymology, vol. 421, 2007, 17-21.
Kitzman, et al., "Hapiotype-resolved genome sequencing of a Gujarati Indian individual", Nature Biotechnology, vol. 29(1), Jan. 2011, 59-63.
Kramer, PR, "cDNA Library Construction from Single Cells", Current Protocols in Neuroscience, 2002, 4.27.1-4.27.19.
Lai et al., "A shotgun optical map of the entire Plasmodium falciparum genome.", Nat Genet. 23(3), 1999, 309-13.
Lander, et al., "Initial sequencing and analysis of the human genome", Nature, 409(6822), 2001, 860-921.
Levy, et al., "The Diploid Genome Sequence of an Individual Human", PLoS Biology, vol. 5, Issue 10, Oct. 2007, 2113-2144.
Li, et al., "Fast and accurate short read alignment with Burrows-Wheeler transform", Bioinformatics 25:1754-1760, 2009.
Li et al., "De novo assembly of human genomes with massively parallel short read sequencing", Genome Res. 20 (2), 2010, 265-72.
Li et al., "Primasebased whole genome amplification", Nucleic Acids Res. 36(13), 2008, e79.
Li et al., "The DNA methylome of human peripheral blood mononuclear cells", PLoS Biol 8(11), 2010, e1000533.
Lieberman-Al Den et al., "Comprehensive mapping of long-range interactions reveals folding principles of the human genome", Science. 326(5950), 2009, 289-93.
Lim et al., "Shotgun optical maps of the whole *Escherichia coli* 0157:H7 genome", Genome Res. 11 (9), 2001, 1584-93.
Lin et al., "Wholegenome shotgun optical mapping of Deinococcus radiodurans.", Science. 285(5433):, 1999, 1558-62.
Lister, et al., "Human DNA methylomes at base resolution show widespread epigenomic differences", Nature, 462(7271), Nov. 19, 2009, 315-322.
Margulies, et al., "Genome sequencing in microfabricated highdensity picolitre reactors", Nature, vol. 437, 2005, 376-380 and Supplemental Materials.
Marine, et al., "Evaluation of a transposase protocol for rapid generation of shotgun high-throughput sequencing libraries from nanogram quantities of DNA", Appl. Environ. Microbial, vol. 77 (22), Nov. 2011, 8071-8079.
Mazutis et al., "Droplet-based microfluidic systems for highthroughput single DNA molecule isothermal amplification and analysis", Anal Chern. 81 (12), 2009, 4813-21.
McCloskey, et al., "Encoding PCR Products with Batch-stamps and Barcodes", Biochem Genet 45:761, Oct. 23, 2007, 761-767.
Meissner, et al., Nucleic Acids Research, 33, 2005, 5868-5877.
Miner, et al., "Molecular barcodes detect redundancy and contamination in hairpin-bisulfite PCR", Nucleic Acids Research, 2004, vol. 32, No. 17, Sep. 30, 2004, el35, 4 pages.
Mitra, Robi D. et al., "Fluorescent in situ sequencing on polymerase colonies", Analytical Biochemistry—320 (2003) 55-65, 2003, 55-65.
Mortazavi, Ali et al., "Mapping and quantifying mammalian transcriptomes by RNA-seq", Nature Methods, 5(7), 2008, 621-8.
Ng et al., "Targeted capture and massively parallel sequencing of 12 human exomes", Nature. 461 (7261), 2009, 272-6.
Numan, et al., "Mutation discovery by targeted genomic enrichment of multiplexed barcoded samples", Nature Methods, vol. 7, No. 11, Nov. 2010, 913-915,.
Oh, et al., "A universal TagModule collection for parallel genetic analysis of microorganisms", Nucleic Acids Research, vol. 38, No. 14, May 21, 2010, 146.
Oh, J. et al., "A Robust Platform for High-Throughput Genomics in Microorganisms", A dissertation submitted to the department of genetics and the committee on graduate studies of Stanford University in partial fulfillment of the requirements for the degree of doctor of philosophy, Mar. 2010, i, ii and 10-30.
Ooka, et al., "Inference of the impact of insertion sequence (IS) elements on bacterial genome diversification through analysis of small size suuctural polymorphisms in *Escherichia coli* 0157 genomes", Genome Research, vol. 19, 2009, 1809-1816.
Paul, et al., "Single-molecule dilution and multiple displacement amplification for molecular haplotyping", BioTechniques 38, Apr. 2005, 553-559.
Pobigaylo, et al., "Construction of a large signature-tagged miniTn5 transposon Tibrary and its application to mutagenesis of Sinorhizobium meliloti". Applied and Environmental Microbiology, vol. 72, No. 6, Jun. 2006, 4329-4337.
Rachel, Marine et al., "Evaluation of a transposase protocol for rapid generation of shotgun high-throughput sequencing libraries from nanogram quantities of DNA", Applied and Environmental Microbiology, vol. 77, No. 22, Nov. 2011, 8071-8079.
Ramanathan, et al., "An integrative approach for the optical sequencing of single DNA molecules", Analytical Biochemistry, vol. 330, No. 2, 2004, 227-241.
Riehn et al., "Restriction mapping in nanofluidic devices.", Proceedings of the National Academy of Sciences of the United States of America 102(29):, 2005, 10012-10016.
Ritz et al., "Structural variation analysis with strobe reads", Bioinformatics. 26(10), 2010, 1291-8.
Savilahti, et al., "The Phage Mu transpososome core: DNA requirements for assembly and function", EMBO J., 14, 1995, 4893-4903.
Schwartz, et al., "Capturing native long-range contiguity by in situ library construction and optical sequencing", PNAS, vol. 109m No. 46, 2012, 18749-18754.
Schwartz et al., "Ordered restriction maps of *Saccharomyces cerevisiae* chromosomes consuucted by optical mapping", Science. 262 (5130), 1993, 110-4.
Shendure, et al., "Accurate Multiplex Polony Sequencing of an Evolved Bacterial Genome", Science, vol. 309, Sep. 9, 2005, 1728-1732.
Shendure, et al., "Advanced sequencing technologies: methods and goals", Nature Rev. Genet., 5, 2004, 335-344.
Shendure, et al., "Next-generation DNA sequencing", Nature Biotechnology 26(10), 2008, 1135-1145.
Shendure, "Sequence Tag Directed Subassembly of Short Sequencing Reads Into Long Sequencing Reads", U.S. Appl. No. 61/096,720, filed Sep. 12, 2008.
Shevchenko, et al., "Systematic sequencing of cDNA clones using the transposon Tn5", Nacl. Acids Res. 30, 2002, 2469-2477.
Sipos, et al., "An Improved Protocol for Sequencing of Repetitive Genomic Regions and Structural Variations Using Mutagenesis and Next Generation Sequencing", PLoS One 7(8), published online doi: 10.1371/journal.pone.0043359, Aug. 17, 2012, e43359.
Steensel et al., "Genomics tools for unraveling chromosome architecture", Nature Bitoechnology, Oct. 13, 2010.
Syed, "Next-generation sequencing library preparation: simultaneous fragmentation and tagging using in vitro transposition", Application Notes, Nature Methods, Epicentre Biotech, Nov. 2009, i-ii.
Syed, Fraz et al., "Optimized library preparation method for next generation sequencing", Nature Methods, 6(10), 2009, 1-11.
Van Berkum et al., "Method to Study the Three-dimensional Architecture of Genomes", http://www.jove.com/details.stp?id-1869 doi:l 0.3791/1869. J Vis Exp.39, (2010).
Wang, et al., "Calling Cards enable multiplexed identification of genomic targets of DNA-binding proteins", Genome Research, vol. 21, No. 5, 2011, 748-755.
Waterston et al., "Initial sequencing and comparative analysis of the mouse genome", Nature. 420(6915), 2002, 520-62.
Waterston et al., "On the sequencing of the human genome", Proc Natl Acad Sci USA. 99(6), 2002, 3712-6.
Xu, J., "Extracting Haplotypes from Diploid Organisms", Current Issues in Molecular Biology, vol. 8, Jul. 2006, 113-122.
Zeevi, et al., "Increasing cloning possibilities using artificial zinc finger nucleases", Proceedings of the National Academy of Sciences, USA, vol. 105, Nov. 35, Sep. 2008, 12785-12790.

(56) References Cited

OTHER PUBLICATIONS

Zeng et al., "High-performance single cell genetic analysis using microfluidic emulsion generator arrays.", Anal Chem. 82 (8), 2010, 3183-90.

Zhou, et al., "Molecular genetic analysis of tarnsposase—end DNA sequence recognition: Cooperativity of three adjacent base-pairs in specific interaction with a mutant Tn5 transposase". Journal of Molecular Biology, vol. 276, 1998, 913-925.

Zhou et al., "A Single Molecule Scaffold for the Maize Genome", PLoS Genet 5(11), 2009, el000711.

Zhou et al., "Validation of rice genome sequence by optical mapping", BMC Genomics 8(1), 2007, 278.

Zilberman et al., "Genome-wide analysis of DNA methylation patterns.", Development 134(22), 2007, 3959-3965.

Examination Report No. 2 for AU Application No. 2019203198, dated May 21, 2021, 5 pgs.

Dienekes' Anthropology Blog, ASHG 2014 Titles and Abstracts, 2014, 1 indicating a publication date of Sep. 2014 for the Book of Abstracts of the 64th Annual Meeting of the American Society of Human Geneteics meeting held Oct. 18-22, 2014 in San Diego, California, 1-12. (Year: 2014).

Fisther et al., "Contiguity Preserving Transposition Sequencing (CPT-seq): Haplotype-Resolved Sequencing and Assembly," Book of Abstracts, Poster Abstract 1698s, 64th Annual Meeting of the American Society of Human Genetics, published Sep. 2014; held Oct. 18-22, 2014, San Diego, California, 1-2. (Year 2014).

Law Insider, "All or Substantially All" Legal Definition, Law Insider, 2020,1-5; obtained from https://www.lawinsider.com/dictionary/all-or-substantially-all on Jun. 23, 2021. (Year: 2013).

Salmen, F., et al., "Barcoded Solid-Phase RNA Capture for Spatial Transcriptomics Profiling in Mammalian Tissue Sections," Nature Protocols 13(11):2501-2534, Nov. 2018.

EP Extended European Search Report in EP Application No. 19183798.8, dated Mar. 12, 2020, 16 pages.

* cited by examiner

METHODS AND COMPOSITIONS FOR NUCLEIC ACID SEQUENCING

FIELD OF THE INVENTION

Embodiments of the present invention relate to sequencing nucleic acids. In particular, embodiments of the methods and compositions provided herein relate to preparing nucleic acid templates and obtaining sequence data therefrom.

BACKGROUND OF THE INVENTION

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of nucleic acids all in a single sequencing run. As such, the information generated from a single sequencing run can be enormous.

SUMMARY OF THE INVENTION

Some embodiments of the methods and compositions provided herein include a method of obtaining sequence information from a target nucleic acid, said method comprising: (a) obtaining a template nucleic acid comprising a plurality of transposomes inserted into said target nucleic acid, wherein at least some of the inserted transposomess each comprise a first transposon sequence, a second transposon sequence noncontiguous with said first transposon sequence, and a transposase associated with the first transposon sequence and the second transposon sequence; (b) compartmentalizing the template nucleic acid comprising said plurality of inserted transposomes into each vessel of a plurality of vessels; (c) removing the transposase from the template nucleic acid; and (d) obtaining sequence information from the template nucleic acid of each vessel.

In some embodiments, step (h) comprises providing each vessel with an amount of template nucleic acid equal to about less than one haploid equivalent, about equal than one haploid equivalent, or more than one haploid equivalent of the target nucleic acid.

In some embodiments, step (b) comprises providing each vessel with an amount of template nucleic acid less than about one haploid equivalent of the target nucleic acid.

In some embodiments, step (c) comprises a method selected from the group consisting of adding a detergent, changing temperature, changing pH, adding a protease, adding a chaperone, and adding a polymerase.

In some embodiments, the first transposon sequence comprises a first primer site and the second transposon sequences comprise a second primer site.

In some embodiments, the first primer site further comprises a first barcode and the second primer site further comprises a second barcode.

In some embodiments, the first barcode and second barcode are different.

In some embodiments, the target nucleic acid comprises an amplified nucleic acid.

In some embodiments, the target nucleic acid is obtained by enriching a plurality of nucleic acids for a sequence of interest before or after transposition.

In some embodiments, step (a) further comprises enriching the template nucleic acid for a sequence of interest.

In some embodiments, the target nucleic acid comprises genomic DNA.

In some embodiments, step (d) further comprises assembling from sequence data a representation of at least a portion of said template nucleic acid from each vessel.

In some embodiments, the sequence information comprises haplotype sequence information.

Some embodiments of the methods and compositions provided herein include a method for preparing a library of template nucleic acids to obtain sequence information from a target nucleic acid, said method comprising: (a) preparing a template nucleic acid comprising a plurality of transposomes inserted into said target nucleic acid, wherein at least some of the inserted transposome each comprise a first transposon sequence, a second transposon sequence noncontiguous with said first transposon sequence, and a transposase associated with the first transposon sequence and the second transposon sequence; and (b) compartmentalizing the template nucleic acid comprising said plurality of inserted transposomes into each vessel of a plurality of vessels; and (c) removing the transposase from the template nucleic acid.

In some embodiments, step (b) comprises providing each vessel with an amount of template nucleic acid equal to less than one haploid equivalent, about one equivalent, or more than one equivalent of the target nucleic acid.

In some embodiments, step (b) comprises providing each vessel with an amount of template nucleic acid less than about one haploid equivalent of the target nucleic acid.

In some embodiments, step (c) comprises a method selected from the group consisting of adding a detergent, changing temperature, changing pH, adding a protease, adding a chaperone, and adding a polymerase.

In some embodiments, the first transposon sequence comprises a first primer site and the second transposon sequences comprise a second primer site.

In some embodiments, the first primer site further comprises a first barcode and the second primer site further comprises a second barcode.

In some embodiments, the first barcode and second barcode are different.

In some embodiments, the target nucleic acid comprises an amplified nucleic acid.

In some embodiments, the target nucleic acid is obtained by enriching a plurality of nucleic acids for a sequence of interest.

In some embodiments, step (a) further comprises enriching the template nucleic acid for a sequence of interest.

In some embodiments, the target nucleic acid comprises genomic DNA.

In some embodiments, the sequence information comprises haplotype sequence information.

Some embodiments of the methods and compositions provided herein include a library of template nucleic acids prepared according to any one of the foregoing methods.

Some embodiments of the methods and compositions provided herein include a method of obtaining sequence information from a target nucleic acid, said method comprising: (a) compartmentalizing the target nucleic acid into a plurality of first vessels; (b) providing a first index to the target nucleic acid of each first vessel, thereby obtaining a first indexed nucleic acid; (c) combining the first indexed nucleic acids; (d) compartmentalizing the first indexed template nucleic acids into a plurality of second vessels; (e) providing a second index to the first indexed template nucleic of each second vessel, thereby obtaining a second indexed nucleic acid; and (f) obtaining sequence information from the second indexed nucleic acid of each second vessel.

In some embodiments, step (b) comprises contacting the target nucleic acid with a plurality of transposomes each comprising a transposase and a transposon sequence comprising the first index under conditions such that at least some of the transposon sequences insert into the target nucleic acid.

In some embodiments, step (b) comprises contacting the target nucleic acid with a plurality of transposomes each transposon comprising a first transposon sequence comprising a first index, a second transposon sequence noncontiguous with said first transposon sequence, and a transposase associated with the first transposon sequence and the second transposon sequence.

In some embodiments, step (d) comprises removing the transposase from the compartmentalized first indexed template nucleic acids.

In some embodiments, the transposase is removed subsequent to step (b).

In some embodiments, the transposase is removed prior to step (f).

In some embodiments, removing the transposase comprises a method selected from the group consisting of adding a detergent, changing temperature, changing pH, adding a protease, adding a chaperone, and adding a strand-displacing polymerase.

In some embodiments, the first transposon sequences comprises a first primer site and the second transposon sequences comprises a second primer site.

In some embodiments, the first primer site further comprises a first barcode and the second primer site further comprises a second barcode.

In some embodiments, the first barcode and second barcode are different.

In some embodiments, step (b) comprises amplifying the target nucleic acid with at least one primer comprising the first index.

In some embodiments, step (b) comprises ligating the target nucleic acid with at least one primer comprising the first index.

In some embodiments, the first index provided to the target nucleic acid of each first vessel is different.

In some embodiments, step (a) comprises providing each first vessel with an amount of target nucleic acid greater than about one or more haploid equivalents of the target nucleic acid.

In some embodiments, step (d) comprises providing each vessel with an amount of the first indexed template nucleic acids greater than about one or more haploid equivalents of the target nucleic acid.

In some embodiments, step (e) comprises amplifying the first indexed template nucleic with at least one primer comprising the second index.

In some embodiments, step (e) comprises ligating the first indexed template nucleic with at least one primer comprising the second index.

In some embodiments, the second index provided to the first indexed template nucleic of each second vessel is different.

In some embodiments, the target nucleic acid comprises an amplified nucleic acid.

In some embodiments, the target nucleic acid is obtained by enriching a plurality of nucleic acids for a sequence of interest.

In some embodiments, the target nucleic acid comprises genomic DNA.

In some embodiments, step (f) further comprises assembling from sequence data a representation of at least a portion of said template nucleic acid from each vessel.

Some embodiments of the methods and compositions provided herein include a method preparing a library of template nucleic acids to obtain sequence information from a target nucleic acid, said method comprising: (a) compartmentalizing the target nucleic acid into a plurality of first vessels; (h) providing a first index to the target nucleic acid of each first vessel, thereby obtaining a first indexed nucleic acid; (c) combining the first indexed nucleic acids; (d) compartmentalizing the first indexed template nucleic acids into a plurality of second vessels; and (e) providing a second index to the first indexed template nucleic of each second vessel, thereby obtaining a second indexed nucleic acid.

In some embodiments, step (b) comprises contacting the target nucleic acid with a plurality of transposomes each comprising a transposase and a transposon sequence comprising the first index under conditions such that at least some of the transposon sequences insert into the target nucleic acid.

In some embodiments, step (b) comprises contacting the target nucleic acid with a plurality of transposomes each transposon comprising a first transposon sequence comprising a first index, a second transposon sequence noncontiguous with said first transposon sequence, and a transposase associated with the first transposon sequence and the second transposon sequence.

In some embodiments, step (d) comprises removing the transposase from the compartmentalized first indexed template nucleic acids.

In some embodiments, removing the transposase comprises a method selected from the group consisting of adding a detergent, changing temperature, changing pH, adding a protease, adding a chaperone, and adding a polymerase.

In some embodiments, the first transposon sequences comprises a first primer site and the second transposon sequences comprises a second primer site.

In some embodiments, the first primer site further comprises a first barcode and the second primer site further comprises a second barcode.

In some embodiments, the first barcode and second barcode are different.

In some embodiments, step (b) comprises amplifying the target nucleic acid with at least one primer comprising the first index.

In some embodiments, step (b) comprises ligating the target nucleic acid with at least one primer comprising the first index.

In some embodiments, the first index provided to the target nucleic acid of each first vessel is different.

In some embodiments, step (a) comprises providing each first vessel with an amount of target nucleic acid greater than about one or more haploid equivalents of the target nucleic acid.

In some embodiments, step (d) comprises providing each vessel with an amount of the first indexed template nucleic acids greater than about one or more haploid equivalents of the target nucleic acid.

In some embodiments, step (e) comprises amplifying the first indexed template nucleic with at least one primer comprising the second index.

In some embodiments, step (e) comprises ligating the first indexed template nucleic with at least one primer comprising the second index.

In some embodiments, the second index provided to the first indexed template nucleic of each second vessel is different.

In some embodiments, the target nucleic acid comprises an amplified nucleic acid.

In some embodiments, the target nucleic acid is obtained by enriching a plurality of nucleic acids for a sequence of interest either before or after transposition.

In some embodiments, the target nucleic acid comprises genomic DNA.

Some embodiments of the methods and compositions provided herein include a library of template nucleic acids prepared according to any one of the foregoing methods.

DETAILED DESCRIPTION

Figure 1:
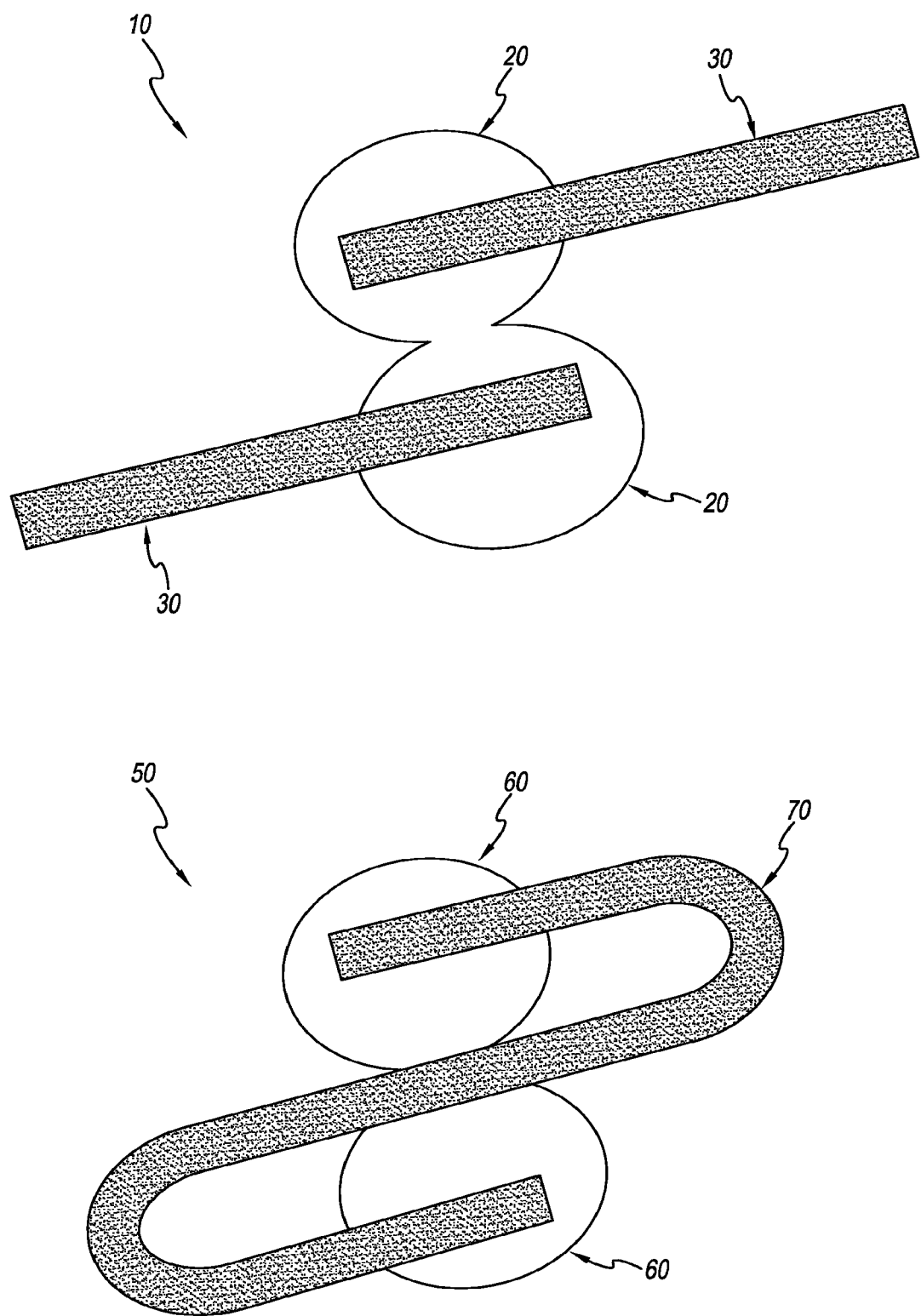
FIG. 1 depicts a schematic of a transposome comprising a dimeric transposase and two non-contiguous transposon sequences, and a transposome comprising a dimeric transposase and a contiguous transposon sequence.

Embodiments of the present invention relate to sequencing nucleic acids. In particular, embodiments of the methods and compositions provided herein relate to preparing nucleic acid templates and obtaining sequence data therefrom. Methods and compositions provided herein are related to the methods and compositions provided in U.S. Patent Application Pub. No. 2012/0208705, U.S. Patent Application Pub. No. 2012/0208724 and Int. Patent Application Pub. No. WO 2012/061832, each of which is incorporated by reference in its entirety. Some embodiments of the present invention relate to preparing templates to obtain haplotype sequence information from a target nucleic acid, and obtaining haplotype sequence information from such templates. More embodiments relate to preparing templates to obtain sequence information from a strand of a double-stranded target nucleic acid, and obtaining sequence information from such templates. Particular embodiments provided herein relate to the use of integrases, for example transposases, to maintain physical proximity of associated ends of fragmented nucleic acids; and to the use of virtual compartments to enable the use of high concentrations of nucleic acids.

Obtaining haplotype information from a target nucleic acid includes distinguishing between different alleles (e.g., SNPs, genetic anomalies, etc.) in a target nucleic acid. Such methods are useful to characterize different alleles in a target nucleic acid, and to reduce the error rate in sequence information. Generally, methods to obtain haplotype sequence information include obtaining sequence information for a portion of a template nucleic acid. In one embodiment, a template nucleic acid can be diluted and sequence information obtained from an amount of template nucleic acid equivalent to about a haplotype of the target nucleic acid.

In further embodiments, a template nucleic acid can be compartmentalized such that multiple copies of a chromosome can be present in the same compartment, as a result of dual or multiple indexing provided herein, a haplotype can still also be determined. In other words, a template nucleic acid can be prepared using virtual compartments. In such embodiments, a nucleic acid can be distributed between several first compartments, providing a first index to the nucleic acid of each compartment, combining the nucleic acids, distributing the nucleic acid between several second compartments, and providing a second index to the nucleic acid of each compartment. Advantageously, such indexing enables haplotype information to be obtained at higher concentrations of nucleic acid compared to the mere dilution of a nucleic acid in a single compartment to an amount equivalent to a haplotype of the nucleic acid.

In some embodiments provided herein, template libraries are prepared using transposomes. In some such libraries, the target nucleic acid may be fragmented. Accordingly, some embodiments provided herein relate to methods for maintaining sequence information for the physical contiguity of adjacent fragments. Such methods include the use of integrases to maintain the association of template nucleic acid fragments adjacent in the target nucleic acid. Advantageously, such use of integrases to maintain physical proximity of fragmented nucleic acids increases the likelihood that fragmented nucleic acids from the same original molecule, e.g, chromosome, will occur in the same compartment.

Other embodiments provided herein relate to obtaining sequence information from each strand of a nucleic acid which can be useful to reduce the error rate in sequencing information. Methods to prepare libraries of template nucleic acids for obtaining sequence information from each strand of a nucleic acid can be prepared such that each strand can be distinguished, and the products of each strand can also be distingguished.

Some of the methods provided herein include methods of analyzing nucleic acids. Such methods include preparing a library of template nucleic acids of a target nucleic acid, obtaining sequence data from the library of template nucleic acids, and assembling a sequence representation of the target nucleic acid from such sequence data.

Generally, the methods and compositions provided herein are related to the methods and compositions provided in U.S. Patent Application Pub. No, 2012/0208705, U.S. Patent Application Pub. No. 2012/0208724 and Int. Patent Application Pub. No. WO 2012/061832, each of which is incorporated by reference in its entirety. The methods provided herein relate to the use of transposomes useful to insert features into a target nucleic acid. Such features including fragmentation sites, primer sites, barcodes, affinity tags, reporter moieties, etc.

In a method useful with the embodiments provided herein, a library of template nucleic acids is prepared from a target nucleic acid. The library is prepared by inserting a plurality of unique barcodes throughout the target nucleic acid. In some embodiments, each barcode includes a first barcode sequence and a second barcode sequence, having a fragmentation site disposed therebetween. The first barcode sequence and second barcode sequence can be identified or designated to be paired with one another. The pairing can be informative so that a first barcode is associated with a second barcode. Advantageously, the paired barcode sequences can be used to assemble sequencing data from the library of template nucleic acids. For example, identifying a first template nucleic acid comprising a first barcode sequence and a second template nucleic acid comprising a second barcode sequence that is paired with the first indicates that the first and second template nucleic acids represent sequences adjacent to one another in a sequence representation of the target nucleic acid. Such methods can be used to assemble a sequence representation of a target nucleic acid de nova, without the requirement of a reference genome.

Definitions

As used herein the term "nucleic acid" and/or "oligonucleotide" and/or grammatical equivalents thereof can refer to at least two nucleotide monomers linked together. A nucleic acid can generally contain phosphodiester bonds; however, in some embodiments, nucleic acid analogs may have other types of backbones, comprising, for example, phosphoramide (Beaucage, et al., *Tetrahedron,* 49:1925 (1993); Letsinger, *J. Org. Chem.,* 35:3800(1970); Sprinzl, et al., *Eur. J. Biochem.,* 81:579(1977); Letsinger, et al., *Nucl. Acids Res.,* 14:3487(1986); Sawai, et al., Chem. Lett., 805 (1984), Letsinger, et al., *J. Am. Chem. Soc.,* 110:4470(1988); and Pauwels, et al., *Chemica Scripta,* 26:141 (1986)), phosphorothioate (Mag, et al., *Nucleic Acids Res.,* 19:1437 (1991); and U.S. Pat. No. 5,644,048), phosphorodithioate (Briu, et al., *J. Am. Chem. Soc.,* 111:2321(1989), O-methylphosphoroamidite linkages (see Eckstein, *Oligonucleotides and Analogues: A Practical Approach,* Oxford University Press), and peptide nucleic acid backbones and linkages (see Egholm, *J. Am. Chem. Soc.,* 114:1895(1992); Meier, et al., *Chem. Int. Ed. Engl.,* 31:1008(1992); Nielsen, *Nature,* 365:566(1993); Carlsson, et al., *Nature,* 380:207 (1996)).

Other analog nucleic acids include those with positive backbones (Denpcy, et al., *Proc. Natl. Acad. Sci. USA,* 92:6097(1995)); non-ionic backbones (U.S. Pat. Nos. 5,386, 023; 5,637,684; 5,602,240; 5,216,141; and 4,469,863; Kiedrowshi, et al., Angew. Chem. Intl. Ed. English. 30:423 (1991); Letsinger, et al., *J. Am. Chem. Soc.* 110:4470(1988); Letsinger, et al., *Nucleosides & Nucleotides,* 13:1597 (1994); Chapters 2 and 3, *ASC Symposium Series* 580, "Carbohydrate Modifications in Antisense Research", Ed. Y. S. Sanghui and P. Dan Cook; Mesmaeker, et al., *Bioorganic & Medicinal Chem. Lett.,* 4:395 (1994); Jeffs, et al., *J. Biomolecular NMR,* 34:17 (1994); *Tetrahedron Lett.,* 37:743 (1996)) and non-ribose (U.S. Pat. Nos. 5,235,033 and 5,034, 506, and Chapters 6 and 7, *ASC Symposium Series* 580, "Carbohydrate Modifications in Antisense Research", Ed. Y. S. Sanghui and P. Dan Coo). Nucleic acids may also contain one or more carbocyclic sugars (see Jenkins, et al., Chem. Soc. Rev., (1995) pp. 169 176).

Modifications of the ribose-phosphate backbone may be done to facilitate the addition of additional moieties such as labels, or to increase the stability of such molecules under certain conditions. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, for example, genomic or cDNA, RNA or a hybrid, from single cells, multiple cells, or from multiple species, as with metagenomic samples, such as from environmental samples, further from mixed samples for example mixed tissue samples or mixed samples for different individuals of the same species, disease samples such as cancer related nucleic acids, and the like. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc.

In some embodiments, a nucleic acid can include at least one promiscuous base. Promiscuous bases can base-pair with more than one different type of base. In some embodiments, a promiscuous base can base-pair with at least two different types of bases and no more than three different types of bases. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole (Loakes et al., *Nucleic. Acid Res.* 22:4039(1994); Van Aerschot et al., *Nucleic Acid Res.* 23:4363(1995); Nichols et al., *Nature* 369:492 (1994); Bergstrom et al., *Nucleic Acid Res.* 25:1935(1997); Loakes et al., Nucleic Acid Res. 23:2361(1995); Loakes et al., *J. Mol. Biol.* 270:426 (1997); and Fotin et al., *Nucleic Acid Res.* 26:1515 (1998)). Promiscuous bases that can base-pair with at least three, four or more types of bases can also be used.

As used herein, the term "nucleotide analog" and/or grammatical equivalents thereof can refer to synthetic analogs having modified nucleotide base portions, modified pentose portions, and/or modified phosphate portions, and, in the case of polynucleotides, modified internucleotide linkages, as generally described elsewhere (e.g., Scheit, Nucleotide Analogs, John Wiley, New York, 1980; Englisch, Angew. *Chem. Ed. Engl.* 30:613-29, 1991; Agarwal, *Protocols for Polynucleotides and Analogs*, Humana Press, 1994; and S. Verma and F. Eckstein, *Ann. Rev. Biochem.* 67; 99-134, 1998). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselcnoate, phosphoroanilothioate, phosphoranilidate, phosphoramidate, boronophosphates, including associated counterions, e.g., $H^+$, $NH_4^+$, $Na^+$, if such counterions are present. Example modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include hut are not limited to, locked nucleic acid (LNA) analogs including without limitation Bz-A-LNA, 5-Me-Bz-C-LNA, dmf-G-LNA, and T-LNA (see, e.g., *The Glen Report*, 16(2): 5, 2003; Koshkin et al., *Tetrahedron* 54:3607-30, 1998), and or 3'-modifications where the 2'- or 3'-position is hydrogen, hydroxy, alkoxy methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, B. P. et al., Organic Chem., 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles. In one class of nucleotide analogs, known as peptide nucleic acids, including pseudocomplementary peptide nucleic acids ("PNA"), a conventional sugar and inter-nucleotide linkage has been replaced with a 2-aminoethylglycine amide backbone polymer (see, e.g., Nielsen et al., *Science*, 254:1497-1500, 1991; Egholm et al., *J. Am. Chem, Soc.,* 114: 1895-1897 1992; Demidov et al., *Proc, Natl. Acad. Sci.* 99:5953-58, 2002; *Peptide Nucleic Acids: Protocols and Applications*, Nielsen, ed., Horizon Bioscience, 2004).

As used herein, the term "sequencing read" and/or grammatical equivalents thereof can refer to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. A sequencing read can be carried out on a single target nucleic acid molecule or simultaneously on a population of target nucleic acid molecules having the same sequence, or simultaneously on a population of target nucleic acids having different sequences. In some embodiments, a sequencing read is terminated when signals are no longer obtained from one or more target nucleic acid molecules from which signal acquisition was initiated. For example, a sequencing read can be initiated for one or more target nucleic acid molecules that are present on a solid phase substrate and terminated upon removal of the one or more target nucleic acid molecules from the substrate. Sequencing can be terminated by otherwise ceasing detection of the target nucleic acids that were present on the substrate when the sequencing run was initiated.

As used herein, the term "sequencing representation" and/or grammatical equivalents thereof can refer to information that signifies the order and type of monomeric units in the polymer. For example, the information can indicate the order and type of nucleotides in a nucleic acid. The information can be in any of a variety of formats including, for example, a depiction, image, electronic medium, series of symbols, series of numbers, series of letters, series of colors, etc. The information can be at single monomer resolution or at lower resolution. An exemplary polymer is a nucleic acid, such as DNA or RNA, having nucleotide units. A series of "A," "T," "G," and "C" letters is a well-known sequence representation for DNA that can be correlated, at single nucleotide resolution, with the actual sequence of a DNA molecule. Other exemplary polymers are proteins having amino acid units and polysaccharides having saccharide units.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

Transposomes

A "transposome" comprises an integration enzyme such as an integrase or transposase, and a nucleic acid comprising an integration recognition site, such as a transposase recognition site. In embodiments provided herein, the transposase can form a functional complex with a transposase recognition site that is capable of catalyzing a transposition reaction. The transposase may bind to the transposase recognition site and insert the transposase recognition site into a target nucleic acid in a process sometimes termed "fragmentation". In some such insertion events, one strand of the transposase recognition site may be transferred into the target nucleic acid. FIG. 1 depicts two examples of transposomes. In one example, a transposome (10) comprises a dimeric transposase comprising two subunits (20), and two non-contiguous transposon sequences (30). In another example, a transposome (50) comprises a transposase comprises a dimeric transposase comprising two subunits (60), and a contiguous transposon sequence (70).

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilabti, H, et al., *EMBO J.*, 14: 4893, 1995). ME sequences can also be used as optimized by a skilled artisan.

More examples of transposition systems that can be used with certain embodiments of the compositions and methods provided herein include *Staphylococcus aureus* Tn552 (Colegio et al., *J. Bacterial.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science.* 271: 1512, 1996; Craig, N L, Review in: *Curr Top Microbial Immunol.*, 204:27-48, 1996), Tn/O and IS10 (Kleckner N, et al., *Curr Top Microbiol Immunol.*, 204:49-82, 1996), Mariner transposase (Lampe D J, et al., *EMBO J.*, 15: 5470-9, 1996), Tc1 (Plasterk R H, *Curr Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA*, 86:2525-9, 1989), and retrotransposon of yeast (Boeke & Corces, *Annu Rev Microbial.* 43:403-34, 1989). More examples include IS5, Tn10, Tn903, IS911, and engineered versions of transposase family enzymes (Zhang et al., (2009) *PLoS Genet.* 5: e1000689. Epub 2009 Oct. 16; Wilson C. et al (2007) *J. Microbial. Methods* 71:332-5).

More examples of integrases that may be used with the methods and compositions provided herein include retroviral integrases and integrase recognition sequences for such retroviral integrases, such as integrases from HIV-1, HIV-2, SIV, PFV-1, RSV.

Transposon Sequences

Some embodiments of the compositions and methods provided herein include transposon sequences. In some embodiments, a transposon sequence includes at least one transposase recognition site. In some embodiments, a transposon sequence includes at least one transposase recognition site and at least one barcode. Transposon sequences useful with the methods and compositions provided herein are provided in U.S. Patent Application Pub. No, 2012/0208705, U.S. Patent Application Pub, No. 2012/0208724 and Int. Patent Application Pub. No. WO 2012/061832, each of which is incorporated by reference in its entirety. In some embodiments, a transposon sequence includes a first transposase recognition site, a second transposase recognition site, and a barcode or barcodes disposed therebetween.

Transposomes with Non-Contiguous Transposon Sequences

Some transposomes provided herein include a transposase comprising two transposon sequences. In some such embodiments, the two transposon sequences are not linked to one another, in other words, the transposon sequences are non-contiguous with one another. Examples of such transposomes are known in the art, see e.g., U.S. Patent Application Pub. No. 2010/0120098, the disclosure of which is incorporated herein by reference in its entirety. FIG. 1 depicts an example transposome (10) comprising a dimeric transposase (20) and two transposon sequences (30).

Looped Structures

In some embodiments, a transposome comprises a transposon sequence nucleic acid that binds two transposase subunits to form a "looped complex" or a "looped transposome." In essence, a transposase complex with contiguous transposons. FIG. 1 depicts an example transposome (50) comprising a dimeric transposase (60) and a transposon sequence (70). Looped complexes can ensure that transposons are inserted into target DNA while maintaining ordering information of the original target DNA and without fragmenting the target DNA. As will be appreciated, looped structures may insert primers, barcodes, indexes and the like into a target nucleic acid, while maintaining physical connectivity of the target nucleic acid. In some embodiments, the transposon sequence of a looped transposome can include a fragmentation site such that the transposon sequence can be fragmented to create a transposome comprising two transposon sequences. Such transposomes are useful to ensuring that neighboring target DNA fragments, in which the transposons insert, receive code combinations that can be unambiguously assembled at a later stage of the assay.

Barcodes

Generally, a barcode can include one or more nucleotide sequences that can be used to identify one or more particular nucleic acids. The barcode can be an artificial sequence, or can be a naturally occurring sequence generated during transposition, such as identical flanking genomic DNA sequences (g-codes) at the end of formerly juxtaposed DNA fragments. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, such as transposomes comprising two non-contiguous transposon sequences, the first transposon sequence comprises a first barcode, and the second transposon sequence comprises a second barcode. In some embodiments, such as in looped transposomes, a transposon sequence comprises a barcode comprising a first barcode sequence and a second barcode sequence. In some of the foregoing embodiments, the first barcode sequence can be identified or designated to be paired with the second barcode sequence. For example, a known first barcode sequence can be known to be paired with a known second barcode sequence using a reference table comprising a plurality of first and second bar code sequences known to be paired to one another.

In another example, the first barcode sequence can comprise the same sequence as the second barcode sequence. In another example, the first barcode sequence can comprise the reverse complement of the second barcode sequence. In some embodiments, the first barcode sequence and the second barcode sequence are different. The first and second barcode sequences may comprise a bi-code.

In some embodiments of compositions and methods described herein, barcodes are used in the preparation of template nucleic acids. As will be understood, the vast number of available barcodes permits each template nucleic acid molecule to comprise a unique identification. Unique identification of each molecule in a mixture of template nucleic acids can be used in several applications. For example, uniquely identified molecules can be applied to identify individual nucleic acid molecules, in samples having multiple chromosomes, in genomes, in cells, in cell types, in cell disease states, and in species, for example, in haplotype sequencing, in parental allele discrimination, in metagenomic sequencing, and in sample sequencing of a genome, Linkers Some embodiments comprising looped transposomes where a transposase is complexed with contiguous transposons include transposon sequences comprising a first barcode sequence and a second barcode sequence having a linker disposed therebetween. In other embodiments, the linker can be absent, or can be the sugar-phosphate backbone that connects one nucleotide to another. The linker can comprise, for example, one or more of a nucleotide, a nucleic acid, a non-nucleotide chemical moiety, a nucleotide analogue, amino acid, peptide, polypeptide, or protein. In preferred embodiments, a linker comprises a nucleic acid. The linker can comprise at least about 1, 2, 3, 4, 5, 6, 7, 8, 9, 10, 11, 12, 13, 14, 15, 16, 17, 18, 19, 20, or more nucleotides. In some embodiments, a linker can comprise at least about 10, 20, 30, 40, 50, 60, 70, 80, 90, 100, 200, 300, 400, 500 or more nucleotides.

In some embodiments, a linker can be amplifiable for example by PCR, rolling circle amplification, strand displacement amplification, and the like. In other embodiments, a linker can comprise non-amplifiable moieties. Examples of non-amplifiable linkers include organic chemical linkers such as alkyl, propyl, PEG; non-natural bases such as IsoC, isoG; or any group that does not amplify in DNA-based amplification schemes. For example, transposons containing isoC, isoG pairs can be amplified with dNTPs mixtures lacking a complementary isoG and isoC, ensuring that no amplification occurs across the inserted transposons.

In some embodiments, the linker comprises a single-stranded nucleic acid. In some embodiments, the linker couples transposon sequences in a 5'-3' orientation, a 5'-5' orientation, or a 3'-3' orientation.

Fragmentation Sites

In some embodiments comprising looped transposomes the linker can comprise a fragmentation site. A fragmentation site can be used to cleave the physical, hut not the informational association between a first barcode sequence and a second barcode sequence. Cleavage may be by biochemical, chemical or other means. In some embodiments, a fragmentation site can include a nucleotide or nucleotide sequence that may be fragmented by various means. For example, a fragmentation site may comprise a restriction endonuclease site; at least one ribonucleotide cleavable with an RNAse; nucleotide analogues cleavable in the presence of certain chemical agent; a diol linkage cleavable by treatment with periodate; a disulphide group cleavable with a chemical reducing agent; a cleavable moiety that may be subject to photochemical cleavage; and a peptide cleavable by a peptidase enzyme or other suitable means, See e.g., U.S. Patent Application Pub. No. 2012/0208705, U.S. Patent Application Pub. No. 2012/0208724 and Int. Patent Application Pub. No. WO 2012/061832, each of which is incorporated by reference in its entirety.

Primer Sites

In some embodiments, a transposon sequence can include a "sequencing adaptor" or "sequencing adaptor site", that is to say a region that comprises one or more sites that can hybridize to a primer. In some embodiments, a transposon sequence can include at least a first primer site useful for amplification, sequencing, and the like. In some embodiments comprising looped transposomes, a linker can include a sequencing adaptor. In more embodiments comprising looped transposomes, a linker comprises at least a first primer site and a second primer site. The orientation of the primer sites in such embodiments can be such that a primer hybridizing to the first primer site and a primer hybridizing to the second primer site are in the same orientation, or in different orientations.

In some embodiments, a linker can include a first primer site, a second primer site having a non-amplifiable site disposed therebetween. The non-amplifiable site is useful to block extension of a polynucleotide strand between the first and second primer sites, wherein the polynucleotide strand hybridizes to one of the primer sites. The non-amplifiable site can also be useful to prevent concatamers. Examples of non-amplifiable sites include a nucleotide analogue, non-nucleotide chemical moiety, amino-acid, peptide, and polypeptide. In some embodiments, a non-amplifiable site comprises a nucleotide analogue that does not significantly base-pair with A, C, G or T. Some embodiments include a linker comprising a first primer site, a second primer site having a fragmentation site disposed therebetween. Other embodiments can use a forked or Y-shaped adapter design useful for directional sequencing, as described in U.S. Pat. No. 7,741,463, the disclosure of which is incorporated herein by reference in its entirety.

Affinity Tags

In some embodiments, a transposon sequence or transposase can include an affinity tag. In some embodiments comprising looped transposomes a linker can comprise an affinity tag. Affinity tags can be useful for a variety of applications, for example the bulk separation of target nucleic acids hybridized to hybridization tags. Additional application include, but are not limited to, using affinity tags for purifying transposase/transposon complexes and transposon inserted target DNA, for example. As used herein, the term "affinity tag" and grammatical equivalents can refer to a component of a multi-component complex, wherein the components of the multi-component complex specifically interact with or bind to each other. For example an affinity tag can include biotin or poly-His that can bind streptavidin or nickel, respectively. Other examples of multiple-component affinity tag complexes are listed, for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

Reporter Moieties

In some embodiments of the compositions and methods described herein, a transposon sequence or transposase can include a reporter moiety. In some embodiments comprising looped transposomes a linker can comprise a reporter moiety. As used herein, the term "reporter moiety" and grammatical equivalents can refer to any identifiable tag, label, or group. The skilled artisan will appreciate that many different species of reporter moieties can be used with the methods and compositions described herein, either individually or in combination with one or more different reporter moieties. In certain embodiments, a reporter moiety can emit a signal. Examples of a signal includes, but is not limited to, a fluorescent, a chemiluminescent, a bioluminescent, a phosphorescent, a radioactive, a calorimetric, an ion activity, an electronic or an electrochemiluminescent signals. Example reporter moieties are listed, for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

Certain Methods of Making Transposon Sequences

The transposon sequences provided herein can be prepared by a variety of methods. Exemplary methods include direct synthesis, hairpin extension methods, and PCR. In some embodiments, transposon sequences may be prepared by direct synthesis. For example, a transposon sequence comprising a nucleic acid may be prepared by methods comprising chemical synthesis. Such methods are well known in the art, e.g., solid phase synthesis using phosphoramidite precursors such as those derived from protected 2'-deoxynucleosides, ribonucleosides, or nucleoside analogues. Example methods of preparing transposon sequencing can be found in, for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

In some embodiments comprising looped transposomes transposon sequences comprising a single stranded linker can be prepared. In some embodiments, the linker couples the transposon sequences of a transposome such that a transposon sequence comprising a first transposase recognition sequence is coupled to a second transposon sequence comprising a second transposase recognition sequence in a 5' to 3' orientation. In some embodiments, the linker couples a transposon sequence comprising a first transposase recognition sequence to a second transposon sequence comprising a second transposase recognition sequence in a 5' to 5' orientation or in a 3' to 3' orientation. Coupling transposon sequences of a transposome in either a 5' to 5' orientation or in a 3' to 3' orientation can be advantageous to prevent transposase recognition elements, in particular mosaic elements (ME or M), from interacting with one another. For example, coupled transposon sequences can be prepared by preparing transposon sequences comprising either an aldehyde group or oxyamine group. The aldehyde and oxyamine groups can interact to form a covalent bond thus coupling the transposon sequences.

Figure 2:
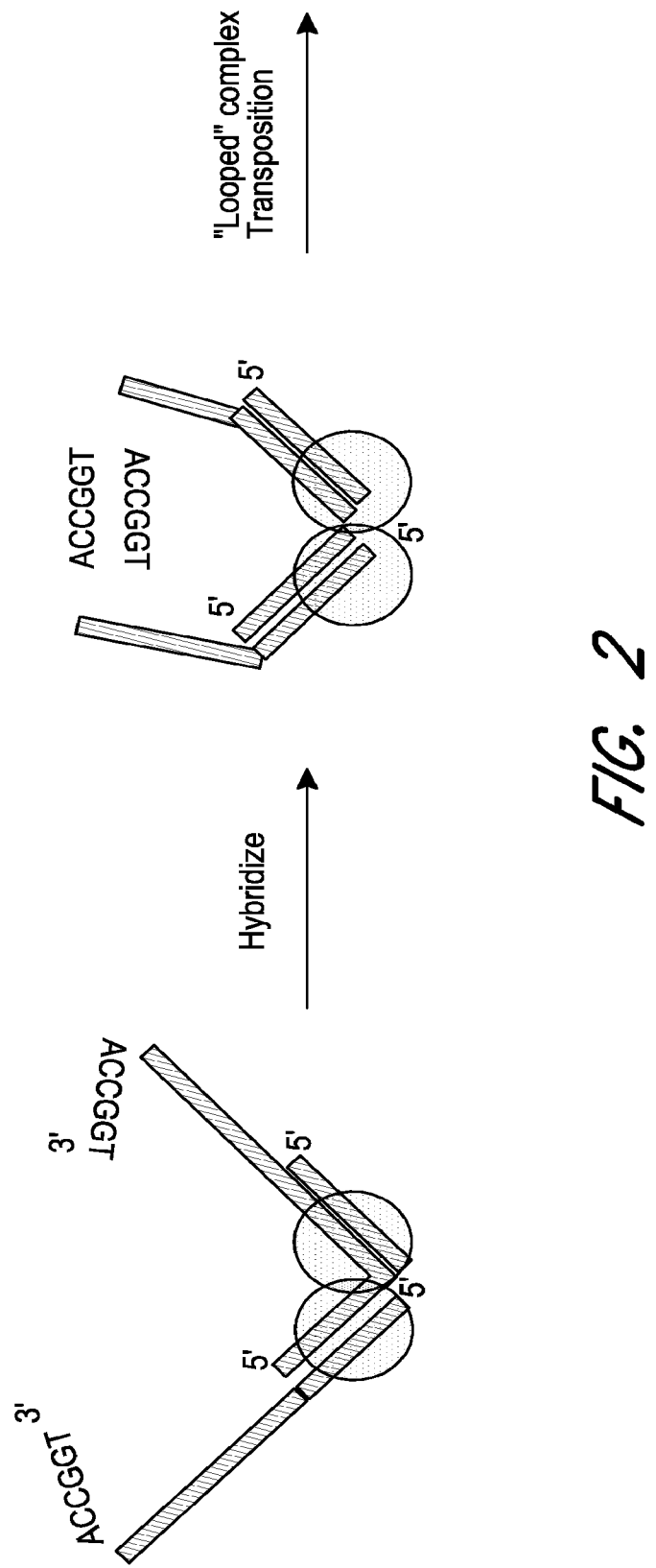
FIG. 2 depicts a method of preparing a transposome with a linker comprising a complementary double-stranded sequence.

In some embodiments, transposomes comprising complementary sequences can be prepared. FIG. 2 illustrates an embodiment in which a transposase is loaded with transposon sequences comprising complementary tails. The tails hybridize to form a linked transposon sequence. Hybridization may occur in dilute conditions to decrease the likelihood of hybridization between transposomes.

Target Nucleic Acids

A target nucleic acid can include any nucleic acid of interest. Target nucleic acids can include DNA, RNA, peptide nucleic acid, morpholino nucleic acid, locked nucleic acid, glycol nucleic acid, threose nucleic acid, mixed samples of nucleic acids, polyploidy DNA (i.e., plant DNA), mixtures thereof, and hybrids thereof. In a preferred embodiment, genomic DNA or amplified copies thereof are used as the target nucleic acid. In another preferred embodiment, cDNA, mitochondrial DNA or chloroplast DNA is used.

A target nucleic acid can comprise any nucleotide sequence. In some embodiments, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500 or 1000 nucleotides or more. Repeat sequences can be repeated, either contiguously or non-contiguously, any of a variety of times including, for example, 2, 3, 4, 5, 6, 7, 8, 9, 10, 15 or 20 times or more.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome.

Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium*, and *Streptomyces* genera); archaeon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (e.g., *Caenorhabditis elegans*), and mammals (for example, rat, mouse, monkey, non-human primate and human): Target nucleic acids and template nucleic acids can be enriched for certain sequences of interest using various methods well known in the art, Examples of such methods are provided in Int, Pub. No. WO/2012/108864, which is incorporated herein by reference in its entirety. In some embodiments, nucleic acids may be further enriched during methods of preparing template libraries. For example, nucleic acids may be enriched for certain sequences, before insertion of transposomes after insertion of transposomes and/or after amplification of nucleic acids.

In addition, in some embodiments, target nucleic acids and/or template nucleic acids can be highly purified, for example, nucleic acids can be at least about 70%, 80%, 90%, 95%, 96%, 97%, 98%, 99%, or 100% free from contaminants before use with the methods provided herein. In some embodiments, it is beneficial to use methods known in the art that maintain the quality and size of the target nucleic acid, for example isolation and/or direct transposition of target DNA may be performed using agarose plugs. Transposition can also be performed directly in cells, with population of cells, lysates, and non-purified DNA.

Certain Methods of Preparing Template Nucleic Acids

Some embodiments include methods of preparing template nucleic acids. As used herein, "template nucleic acid" can refer to a substrate for obtaining sequence information. In some embodiments, a template nucleic acid can include a target nucleic acid, a fragment thereof, or any copy thereof comprising at least one transposon sequence, a fragment thereof, or any copy thereof. In some embodiments, a template nucleic acid can include a target nucleic acid comprising a sequencing adaptor, such as a sequencing primer site.

Some methods of preparing template nucleic acids include inserting a transposon sequence into a target nucleic acid, thereby preparing a template nucleic acid. Some methods of insertion include contacting a transposon sequence provided herein with a target nucleic acid in the presence of an enzyme, such as a transposase or integrase, under conditions sufficient for the integration of the transposon sequence or sequences into the target nucleic acid.

In some embodiments, insertion of transposon sequences into a target nucleic acid can be non-random, hi some embodiments, transposon sequences can be contacted with target nucleic acids comprising proteins that inhibit integration at certain sites. For example, transposon sequences can be inhibited from integrating into genomic DNA comprising proteins, genomic DNA comprising chromatin, genomic DNA comprising nucleosomes, or genomic DNA comprising histones. In some embodiments, transposon sequences can be associated with affinity tags in order to integrate the transposon sequence at a particular sequence in a target nucleic acid. For example, a transposon sequence may be associated with a protein that targets specific nucleic acid sequences, e.g., histones, chromatin-binding proteins, transcription factors, initiation factors, etc., and antibodies or antibody fragments that bind to particular sequence-specific nucleic-acid-binding proteins. In an exemplary embodiment, a transposon sequence is associated with an affinity tag, such as biotin; the affinity tag can be associated with a nucleic-acid-binding protein.

It will be understood that during integration of some transposon sequences into a target nucleic acid, several consecutive nucleotides of the target nucleic acid at the integration site are duplicated in the integrated product. Thus the integrated product can include a duplicated sequence at each end of the integrated sequence in the target nucleic acid. As used herein, the term "host tag" or "g-tag" can refer to a target nucleic acid sequence that is duplicated at each end of an integrated transposon sequence. Single-stranded portions of nucleic acids that may be generated by the insertion of transposon sequences can be repaired by a variety of methods well known in the art, for example by using ligases, oligonucleotides and/or polymerases.

In some embodiments, a plurality of the transposon sequences provided herein is inserted into a target nucleic acid. Some embodiments include selecting conditions sufficient to achieve integration of a plurality of transposon sequences into a target nucleic acid such that the average distance between each integrated transposon sequence comprises a certain number of consecutive nucleotides in the target nucleic acid.

Some embodiments include selecting conditions sufficient to achieve insertion of a transposon sequence or sequences into a target nucleic acid, but not into another transposon sequence or sequences. A variety of methods can be used to reduce the likelihood that a transposon sequence inserts into another transposon sequence. Examples of such methods useful with the embodiments provided herein can be found in for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

In some embodiments, conditions may be selected so that the average distance in a target nucleic acid between integrated transposon sequences is at least about 5, 10, 20, 30, 40, 50, 60, 70, 80, 90, 100, or more consecutive nucleotides. In some embodiments, the average distance in a target nucleic acid between integrated transposon sequences is at least about 100, 200, 300, 400, 500, 600, 700, 800, 900, 1000, or more consecutive nucleotides. In some embodiments, the average distance in a target nucleic acid between integrated transposon sequences is at least about 1 kb, 2 kb, 3 kb, 4 kb, 5 kb, 6 kb, 7 kb, 8 kb, 90 kb, 100 kb, or more consecutive nucleotides. In some embodiments, the average distance in a target nucleic acid between integrated transposon sequences is at least about 100 kb, 200 kb, 300 kb, 400 kb, 500 kb, 600 kb, 700 kb, 800 kb, 900 kb, 1000 kb, or more consecutive nucleotides. As will be understood, some conditions that may be selected include contacting a target nucleic acid with a certain number of transposon sequences.

Some embodiments of the methods described herein include selecting conditions sufficient to achieve at least a portion of transposon sequences integrated into a target nucleic acid that are different. In preferred embodiments of the methods and compositions described herein, each transposon sequence integrated into a target nucleic acid is different. Some conditions that may be selected to achieve a certain portion of transposon sequences integrated into target sequences that are different include selecting the degree of diversity of the population of transposon sequences. As will be understood, the diversity of transposon sequences arises in part due to the diversity of the barcodes of such transposon sequences. Accordingly, some embodiments include providing a population of transposon sequences in which at least a portion of the barcodes are different. In some embodiments, at least about 10%, 20%, 30%, 40%, 50%, 60%, 70%, 80%, 90%, 95%, 98%, 99%, or 100% of barcodes in a population of transposon sequences are different. In some embodiments, at least a portion of the transposon sequences integrated into a target nucleic acid are the same.

Some embodiments of preparing a template nucleic acid can include copying the sequences comprising the target nucleic acid. For example, some embodiments include hybridizing a primer to a primer site of a transposon sequence integrated into the target nucleic acid. In some such embodiments, the primer can be hybridized to the primer site and extended. The copied sequences can include at least one barcode sequence and at least a portion of the target nucleic acid. In some embodiments, the copied sequences can include a first barcode sequence, a second barcode sequence, and at least a portion of a target nucleic acid disposed therebetween. In some embodiments, at least one copied nucleic acid can include at least a first barcode sequence of a first copied nucleic acid that can be identified or designated to be paired with a second barcode sequence of a second copied nucleic acid. In some embodiments, the primer can include a sequencing primer. In some embodiments sequencing data is obtained using the sequencing primer. In more embodiments, adaptors comprising primer sites can be ligated to each end of a nucleic acid, and the nucleic amplified from such primer sites.

Some embodiments of preparing a template nucleic acid can include amplifying sequences comprising at least a portion of one or more transposon sequences and at least a portion of a target nucleic acid. In some embodiments, at least a portion of a target nucleic acid can be amplified using primers that hybridize to primer sites of integrated transposon sequences integrated into a target nucleic acid. In some such embodiments, an amplified nucleic acid can include a first barcode sequence, and second barcode sequence having at least a portion of the target nucleic acid disposed therebetween. In some embodiments, at least one amplified nucleic acid can include at least a first barcode sequence of a first amplified nucleic acid that can be identified to be paired with a second barcode sequence of a second amplified sequence.

Figure 3:
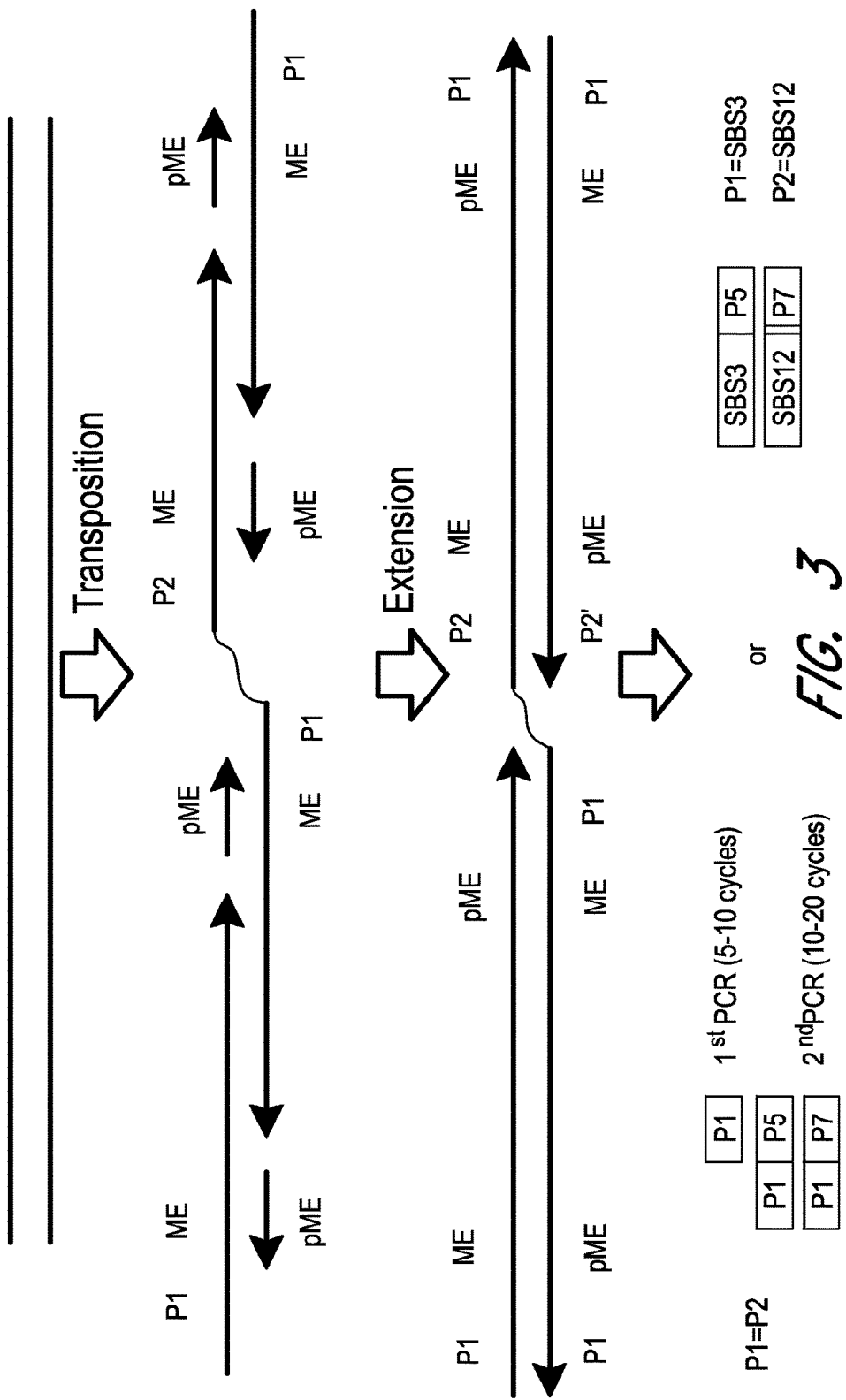
FIG. 3 depicts an embodiment of making a template library using transposomes comprising transposon sequences comprising a single stranded linker coupling the two transposon sequences in each transposome in a 5'-5' orientation. Sequences are extended using primers

Some methods of preparing template nucleic acids include inserting transposon sequences comprising single-stranded linkers. FIG. 3 illustrates an example in which transposon sequences (ME-P1-linker-P2-ME; mosaic end-primer site 1-linker-primer site 2-mosaic end) are inserted into a target nucleic acid. The target nucleic acid having the inserted transposon/linker sequences can be extended and amplified.

In one embodiment of the compositions and methods described herein, transposomes are used that have symmetrical transposable end sequences to produce an end-tagged target nucleic acid fragment (tagmented fragment or tagment). Each tagmented fragment therefore contains identical ends, lacking directionality. A single primer PCR, using the transposon end sequences, can then be employed to amplify the template copy number from 2n to $2n*2^x$ where x corresponds to the number of PCR cycles. In a subsequent step, PCR with primers can add additional sequences, such as sequencing adapter sequences.

In some embodiments, it can be advantageous for each template nucleic acid to incorporate at least one universal primer site. For example, a template nucleic, acid can include first end sequences that comprise a first universal primer site, and second end sequences that comprise a second universal primer site. Universal primer sites can have various applications, such as use in amplifying, sequencing, and/or identifying one or more template nucleic acids. The first and second universal primer sites can be the same, substantially similar, similar, or different. Universal primer sites can be introduced into nucleic acids by various methods well known in the art, for example, ligation of primer sites to nucleic acids, amplification of nucleic acids using tailed primers, and insertion of a transposon sequence comprising a universal primer site.

Targeted Insertion

In some embodiments of the methods and compositions provided herein, transposon sequences may be inserted at particular targeted sequences of a target nucleic acid. Transposition into dsDNA can be more efficient than into ssDNA targets. In some embodiments, dsDNA is denatured into ssDNA and annealed with oligonucleotide probes (20-200 bases). These probes create sites of dsDNA that can be efficiently used as integration sites with transposomes provided herein. In some embodiments, dsDNA can be targeted using D-loop formation with recA-coated oligo probes, and subsequent triplex formation. In some such embodiments, the replication fork structure is the preferred substrate for transposomes comprising Tn4430 transposase. In more embodiments, regions of interest in dsDNA can be targeted using sequence-specific DNA binding proteins such as zinc-finger complexes, and other affinity ligands to specific DNA regions.

In some embodiments, transposomes comprising a transposase having a preferred substrate of mismatched positions in a target nucleic acid may be used to target insertion into the target nucleic acid. For example, some MuA transposases, such as HYPERMU (Epicenter), have a preference for mismatched targets. In some such embodiments, oligonucleotide probes comprising a mismatch are annealed to a single-stranded target nucleic acid. Transposomes comprising MuA transposases, such as HYPERMU, can be used to target the mismatched sequences of the target nucleic acid.

Fragmenting Template Nucleic Acids

Some embodiments of preparing a template nucleic acid can include fragmenting a target nucleic acid. In some embodiments, insertion of transposomes comprising non-contiguous transposon sequences can result in fragmentation of a target nucleic acid. In some embodiments comprising looped transposomes a target nucleic acid comprising transposon sequences can be fragmented at the fragmentation sites of the transposon sequences. Further examples of method useful to fragment target nucleic acids useful with the embodiments provided herein can be found in for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

Tagging Single Molecules

The present invention provides methods for tagging molecules so that individual molecules can be tracked and identified. The bulk data can then be deconvoluted and converted back to the individual molecule. The ability to distinguish individual molecules and relate the information back to the molecule of origin is especially important when processes from original molecule to final product change the (stoichiometric) representation of the original population. For example, amplification leads to duplication (e.g., PCR duplicates or biased amplification) that can skew the original representation. This can alter the methylation state call, copy number, allelic ratio due to non-uniform amplification and/or amplification bias. By identifying individual molecules, code-tagging distinguishes between identical molecules after processing. As such, duplications, and amplification bias can be filtered out, allowing accurate determination of the original representation of a molecule or population of molecules.

An advantage of uniquely tagging single molecules is that identical molecules in the original pool become uniquely identified by virtue of their tagging. In further downstream analyses, these uniquely tagged molecules can now be distinguished. This technique can be exploited in assay schemes in which amplification is employed. For example, amplification is known to distort the original representation of a mixed population of molecules. If unique tagging were not employed, the original representation (such as copy number or allelic ratio) would need to account for the biases (known or unknown) for each molecule in the representation. With unique tagging, the representation can accurately be determined by removing duplicates and counting the original representation of molecules, each having a unique tag. Thus, cDNAs can be amplified and sequenced, without fear of bias because the data can be filtered so that only authentic sequences or sequences of interest are selected for further analysis. Accurate reads can be constructed by taking the consensus across many reads with the same barcode.

In some embodiments of the compositions and methods described herein, it is preferred to tag the original population in the early stages of the assay, although tagging can occur at later stages if the earlier steps do not introduce bias or are not important. In any of these applications, the complexity of the barcode sequences should be larger than the number of individual molecules to be tagged. This ensures that different target molecules receive different and unique tags. As such, a pool of random oligonucleotides of a certain length (e.g., 5, 10, 20, 30, 40, 50, 100 or 200 nucleotides in length) is desirable. A random pool of tags represents a large complexity of tags with code space $4^n$ where n is the number of nucleotides. Additional codes (whether designed or random) can be incorporated at different stages to serve as a further check, such as a parity check for error correction.

In one embodiment of the compositions and methods described herein, individual molecules (such as target DNA) are attached to unique labels, such as unique oligo sequences and/or barcodes. Attachment of the labels can occur through ligation, coupling chemistry, adsorption, insertion of transposon sequences, etc. Other means include amplification (such as by PCR, RCA or LCR), copying (such as addition by a polymerase), and non-covalent interactions.

Specific methods comprise including barcodes (e.g., designed or random sequences) to PCR primers so that each template will receive an individual code within the code space, thereby yielding unique amplicons that can be discriminated from other amplicons. This concept can be applied to any method that uses polymerase amplification, such as GoldenGate assays as disclosed in U.S. Pat. Nos. 7,582,420, 7,955,794, and 8,003,354, each of which is incorporated by reference in its entirety. Code-tagged target sequences can be circularized and amplified by methods such as rolling-circle amplification to yield code-tagged amplicons. Similarly, the code can also be added to RNA Methods of Analyzing Template Nucleic Acids Some embodiments of the technology described herein include methods of analyzing template nucleic acids. In such embodiments, sequencing information can be obtained from template nucleic acids and this information can be used to generate a sequence representation of one or more target nucleic acids.

In some embodiments of the sequencing methods described herein, a linked read strategy may be used. A linked read strategy can include identifying sequencing data that links at least two sequencing reads. For example, a first sequencing read may contain a first marker, and a second sequencing read may contain a second market. The first and second markers can identify the sequencing data from each sequencing read to be adjacent in a sequence representation of the target nucleic acid. In some embodiments of the compositions and methods described herein, markers can comprise a first barcode sequence and a second barcode sequence in which the first barcode sequence can be paired with the second barcode sequence. In other embodiments, markers can comprise a first host tag and a second host tag. In more embodiments, markers can comprise a first barcode sequence with a first host tag, and a second barcode sequence with a second host tag.

An exemplary embodiment of a method for sequencing a template nucleic acid can comprise the following steps: (a) sequence the first barcode sequence using a sequencing primer hybridizing to the first primer site; and (b) sequence the second barcode sequence using a sequencing primer hybridizing to the second primer. The result is two sequence reads that help link the template nucleic acid to its genomic neighbors. Given long enough reads, and short enough library fragments, these two reads can be merged informatically to make one long read that covers the entire fragment. Using the barcode sequence reads and the 9 nucleotide duplicated sequence present from the insertion, reads can now be linked to their genomic neighbors to form much longer "linked reads" in silico.

As will be understood, a library comprising template nucleic acids can include duplicate nucleic acid fragments. Sequencing duplicate nucleic acid fragments is advantageous in methods that include creating a consensus sequence for duplicate fragments. Such methods can increase the accuracy for providing a consensus sequence for a template nucleic acid and/or library of template nucleic acids.

In some embodiments of the sequencing technology described herein, sequence analysis is performed in real time. For example, real time sequencing can be performed by simultaneously acquiring and analyzing sequencing data. In some embodiments, a sequencing process to obtain sequencing data can be terminated at various points, including after at least a portion of a target nucleic acid sequence data is obtained or before the entire nucleic acid read is sequenced. Exemplary methods, systems, and further embodiments are provided in International Patent Publication No. WO 2010/062913, the disclosure of which is incorporated herein by reference in its entirety.

In an exemplary embodiment of a method for assembling short sequencing reads using a linked read strategy, transposon sequences comprising barcodes are inserted into genomic DNA, a library is prepared and sequencing data is obtained for the library of template nucleic acids. Blocks of templates can be assembled by identifying paired barcodes and then larger contigs are assembled. In one embodiment, the assembled reads can be further assembled into larger contigs through code pairing using overlapping reads.

Some embodiments of the sequencing technology described herein include error detection and correction features. Examples of errors can include errors in base calls during a sequencing process, and errors in assembling fragments into larger contigs. As would be understood, error detection can include detecting the presence or likelihood of errors in a data set, and as such, detecting the location of an error or number of errors may not be required. For error correction, information regarding the location of an error and/or the number of errors in a data set is useful. Methods for error correction are well known in the art. Examples include the use of hamming distances, and the use of a checksum algorithm (See, e.g., U.S. Patent Application Publication No. 2010/0323348; U.S. Pat. Nos. 7,574,305; and 6,654,696, the disclosures of which are incorporated herein by reference in their entireties).

Nested Libraries

An alternative method involves the junction tagging methods above and preparation of nested sequencing libraries. The nested sub-libraries are created from code-tagged DNA fragments. This can allow less frequent transposon tagging across the genome. It can also create a larger diversity of (nested) sequencing reads. These factors can lead to improved coverage and accuracy.

Sub-sampling and whole genome amplification can create many copies of a certain population of starting molecules. DNA fragments are then generated by transposon-specific fragmentation, where each fragment receives a code that allows one to link the fragment back to the original neighbor having a matching code (whether identical, complementary or otherwise informatically linked). The tagged fragments are fragmented at least a second time by random methods or sequence-specific methods, such as enzymatic digestion, random shearing, transposon-based shearing or other methods, thereby creating sub-libraries of the code-tagged DNA fragments. In a useful variation of the previously-described method, code-tagged fragments can be preferentially isolated by using transposons that contain a biotin or other affinity functionality for downstream enrichment purposes. Subsequent library preparation converts the nested DNA fragments into sequencing templates. Paired-end sequencing results in determination of the sequence of the code-tag of the DNA fragments and of the target DNA. Since nested libraries for the same code-tag are created, long DNA fragments can be sequenced with short reads.

Sequencing Methods

The methods and composition described herein can be used in conjunction with a variety of sequencing techniques. In some embodiments, the process to determine the nucleotide sequence of a target nucleic acid can be an automated process.

Some embodiments of the sequencing methods described herein include sequencing by synthesis (SBS) technologies, for example, pyrosequencing techniques. Pyrosequencing detects the release of inorganic pyrophosphate ($PP_i$) as particular nucleotides are incorporated into the nascent strand (Ronaghi et al., *Analytical Biochemistry* 242(1): 84-9 (1996); Ronaghi, M. *Genome Res.* 11(1):3-11 (2001); Ronaghi et al., *Science* 281(5375):363 (1998); U.S. Pat. Nos. 6,210,891; 6,258,568 and 6,274,320, each of which is incorporated by reference in its entirety).

In another example type of SBS, cycle sequencing is accomplished by stepwise addition of reversible terminator nucleotides containing, for example, a cleavable or photobleachable dye label as described, for example, in U.S. Pat. No. 7,427,67, U.S. Pat. No. 7,414,1163 and U.S. Pat. No. 7,057,026, each of which is incorporated by reference in its entirety. This approach, which is being commercialized by Illumina Inc., is also described in International Patent Application Publication Nos. WO 91/06678 and WO 07/123744, each of which is incorporated by reference in its entirety. The availability of fluorescently-labeled terminators, in which both the termination can be reversed and the fluorescent label cleaved, facilitates efficient cyclic reversible termination (CRT) sequencing. Polymerases can also be co-engineered to efficiently incorporate and extend from these modified nucleotides.

Additional exemplary SBS systems and methods which can be utilized with the methods and compositions described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No, 2005/0100900, PCT Publication No. WO 06/064199 and PCT Publication No. WO 07/010251, each of which is incorporated by reference in its entirety.

Some embodiments of the sequencing technology described herein can utilize sequencing by ligation techniques. Such techniques utilize DNA ligase to incorporate nucleotides and identify the incorporation of such nucleotides. Exemplary SBS systems and methods which can be utilized with the compositions and methods described herein are described in U.S. Pat. Nos. 6,969,488, 6,172,218, and 6,306,597, each of which is incorporated by reference in its entirety.

Some embodiments of the sequencing technology described herein can include techniques such as next-next technologies. One example can include nanopore sequencing techniques (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis". *Acc. Chem. Res.* 35:817-825 (2002); Li et al., "DNA molecules and configurations in a solid-state nanopore microscope" *Nat. Mater.* 2:611-615 (2003), each of which is incorporated by reference in its entirety). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni & Meller, "A. Progress toward ultrafast DNA sequencing using solid-state nanopores," *Clin. Chem.* 53, 1996-2001 (2007); Healy, K. "Nanopore-based single-molecule DNA analysis," *Nanomed.* 2:459-481 (2007); Cockroft et al., "A single-molecule nanopore device detects DNA polymerase activity with single-nucleotide resolution." *J. Am. Chem. Soc.* 130: 818-820 (2008), each of which is incorporated by reference in its entirety). In some such embodiments, nanopore sequencing techniques can be useful to confirm sequence information generated by the methods described herein.

Some embodiments of the sequencing technology described herein can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 or nucleotide incorporations can be detected with zero-mode waveguides as described, for example, in U.S. Pat. No. 7,315,019 and using fluorescent nucleotide analogs and engineered polymerases as described, for example, in U.S. Pat. No. 7,405,281 and U.S. Patent Application Publication No. 2008/0108082, each of which is incorporated by reference in its entirety. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J, et al. "Selective aluminum passivation for targeted immobilization of single DNA polymerase molecules in zero-mode waveguide nanostructures," *Proc. Natl. Acad. Sci. USA* 105, 1176-1181 (2008), each of which is incorporated by reference in its entirety). In one example, single molecule, real-time (SMRT) DNA sequencing technology provided by Pacific Biosciences Inc. can be utilized with the methods described herein. In some embodiments, a SMRT chip or the like may be utilized (e.g., U.S. Pat. Nos. 7,181,122, 7,302,146 and 7,313,308, each of which is incorporated by reference in its entirety). A SMRT chip comprises a plurality of zero-mode waveguides (ZMW). Each ZMW comprises a cylindrical hole tens of nanometers in diameter perforating a thin metal film supported by a transparent substrate. When the ZMW is illuminated through the transparent substrate, attenuated light may penetrate the lower 20-30 nm of each ZMW creating a detection volume of about $1 \times 10^{-21}$ L. Smaller detection volumes increase the sensitivity of detecting fluorescent signals by reducing the amount of background that can be observed.

SMRT chips and similar technology can be used in association with nucleotide monomers fluorescently labeled on the terminal phosphate of the nucleotide (Korlach J, et al., "Long, processive enzymatic DNA synthesis using 100% dye-labeled terminal phosphate-linked nucleotides." Nucleosides, Nucleotides and Nucleic Acids, 27:1072-1083, 2008, which is incorporated by reference in its entirety). The label is cleaved from the nucleotide monomer on incorporation of the nucleotide into the polynucleotide. Accordingly, the label is not incorporated into the polynucleotide, increasing the signal: background ratio. Moreover, the need for conditions to cleave a label from labeled nucleotide monomers is reduced.

An additional example of a sequencing platform that may be used in association with some of the embodiments described herein is provided by Helicos Biosciences Corp. In some embodiments, TRUE SINGLE MOLECULE SEQUENCING can be utilized (Harris T. D. et al., "Single Molecule DNA Sequencing of a viral Genome" *Science* 320:106-109 (2008), which is incorporated by reference in its entirety). In one embodiment, a library of target nucleic acids can be prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid. In one embodiment, fluorescently-labeled nucleotide monomers, namely, A, C, G, or T, are delivered one at a time to the target nucleic acid in the presence DNA polymerase. Incorporation of a labeled nucleotide into the polynucleotide complementary to the target nucleic acid is detected, and the position of the fluorescent signal on the glass cover slip indicates the molecule that has been extended. The fluorescent label is removed before the next nucleotide is added to continue the sequencing cycle. Tracking nucleotide incorporation in each polynucleotide strand can provide sequence information for each individual target nucleic acid.

An additional example of a sequencing platform that can be used in association with the methods described herein is provided by Complete Genomics Inc. Libraries of target nucleic acids can be prepared where target nucleic acid sequences are interspersed approximately every 20 bp with adaptor sequences. The target nucleic acids can be amplified using rolling circle replication, and the amplified target nucleic acids can be used to prepare an array of target nucleic acids. Methods of sequencing such arrays include sequencing by ligation, in particular, sequencing by combinatorial probe-anchor ligation (cPAL).

In some embodiments using cPAL, about 10 contiguous bases adjacent to an adaptor may be determined. A pool of probes that includes four distinct labels for each base (A, C, T, G) is used to read the positions adjacent to each adaptor. A separate pool is used to read each position. A pool of probes and an anchor specific to a particular adaptor is delivered to the target nucleic acid in the presence of ligase. The anchor hybridizes to the adaptor, and a probe hybridizes to the target nucleic acid adjacent to the adaptor. The anchor and probe are ligated to one another. The hybridization is detected and the anchor-probe complex is removed. A different anchor and pool of probes is then delivered to the target nucleic acid in the presence of ligase.

The sequencing methods described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically coupled to a surface in a spatially distinguishable manner. For example, the target nucleic acids can be bound by direct covalent attachment, attachment to a bead or other particle or associated with a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, $10^7$ features/cm$^2$, $5 \times 10^7$ features/cm$^2$, $10^8$ features/cm$^2$, $5 \times 10^8$ features/cm$^2$, $10^9$ features/cm$^2$, $5 \times 10^9$ features/cm$^2$, or higher.

Surfaces

In some embodiments, the nucleic acid template provided herein can be attached to a solid support ("substrate"). Substrates can be two-or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluiclic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like. Various methods well known in the art can be used to attach, anchor or immobilize nucleic acids to the surface of the substrate.

Methods for Reducing Error Rates in Sequencing Data

Some embodiments of the methods and compositions provided herein include reducing the error rates in sequencing data. In some such embodiments, the sense and antisense strands of a double-stranded target nucleic acid are each associated with a different barcode. Each strand is amplified, sequence information is obtained from multiple copies of the amplified strands, and a consensus sequence representation of the target nucleic acid is generated from the redundant sequence information. Thus, sequence information can originate and be identified from each strand. Accordingly, sequence errors can be identified and reduced where sequence information originating from one strand is inconsistent with sequence information from the other strand.

In some embodiments, the sense and antisense strands of a target nucleic acid are associated with a different barcode. The barcodes may be associated with the target nucleic acid by a variety of methods including ligation of adaptors and insertion of transposon sequences. In some such embodiments, a Y-adaptor may be ligated to at least one end of a target nucleic acid. The Y-adaptor can include a double-stranded sequence, and non-complementary strands, each strand comprising a different barcode. The target nucleic acid with ligated Y-adaptor can be amplified and sequenced such that each barcode can be used to identify the original sense or antisense strands. A similar method is described in Kinde I. et al., (2011) PNAS 108:9530-9535, the disclosure of which is incorporated herein by reference in its entirety. In some embodiments, the sense and antisense strands of a target nucleic acid are associated with a different barcode by inserting transposon sequences provided herein. In some such embodiments, the transposon sequences can comprise non-complementary barcodes.

Some embodiments of such methods include obtaining sequence information from a strand of a target double-stranded nucleic acid comprising (a) obtaining sequence data from a template nucleic acid comprising a first sequencing adapter and a second sequencing adapter having at least a portion of the double-stranded target nucleic acid disposed therebetween, wherein: (i) the first sequencing adapter comprises a double-stranded first barcode, a single-stranded first primer site and a single-stranded second primer site, wherein the first and second primer sites are non-complementary, and (ii) the second sequencing adapter comprising a double-stranded second barcode, a single-stranded third primer site and a single-stranded fourth primer site, wherein the third and fourth primer sites are non-complementary. In some embodiments, the first primer site of the sense strand of the template nucleic acid and the third primer site of the antisense sense strand of the template nucleic acid comprise the same sequence. In some embodiments, each barcode is different. In some embodiments, the first sequencing adapter comprises a single-stranded hairpin coupling the first primer site and second primer site.

In another embodiment, each end of a target nucleic acid is associated with an adaptor comprising a different barcode such that extension products from the sense and antisense strand of a nucleic acid can be distinguished from each other. In some embodiments, primer site sequences and barcodes are selected such that extension from a primer annealed to the sense strand yields products that can be distinguished from products of extension from a primer annealed to the antisense strand. In an example, the 3' sense primer site is the same as the 3' antisense primer site, but different from both the 5' sense and 5' antisense primer sites. Extension of primers annealed to the 3' sense primer site and the 3' antisense primer site would yield the following products from each strand:

Sense strand: (5') barcode 2-[target sequence]-barcode 1 (3')

Antisense strand: (5') barcode 1-[target sequence]-barcode 2 (3')

Thus, extension products from the sense and antisense strand of a nucleic acid can be distinguished from each other. An exemplary method is illustrated in Schmitt M. W., et al., PNAS (2012) 109:14508-13, the disclosure of which is incorporated herein by reference in its entirety. In some such methods, the barcodes and primers sites may be associated with the target nucleic acid by a variety of methods including ligation of adaptors and insertion of transposon sequences. In some embodiments, transposon sequences can be designed to provide adaptors with hairpins. Hairpins provide the ability to maintain the physical contiguity of the sense and antisense strands of a target nucleic acid. A template nucleic acid can be prepared comprising hairpins using transposon sequences comprising linkers described herein. Examples of linkers include single-stranded nucleic acids.

Some embodiments of preparing a library of template nucleic acids for obtaining sequence information from each strand of a double-stranded target nucleic acid include (a) providing a population of transposomes comprising a transposase and a first transposon sequence comprising: (i) a first transposase recognition site, a first primer site, and a first barcode, and (ii) a second transposon sequence comprising a second transposase recognition site, a second primer site, and a second barcode, wherein the first transposon sequence is non-contiguous with the second transposon sequence; and (b) contacting the transposomes with a double-stranded nucleic acid under conditions such that said first and second transposon sequences insert into the double-stranded target nucleic acid, thereby preparing a library of template nucleic acids for obtaining sequence information from each strand of the double-stranded target nucleic acid. In some embodiments, the population of transposomes further comprises transposomes comprising a transposase and a transposon sequence comprising a third transposase recognition site and a fourth transposase recognition site having a barcode sequence disposed therebetween, said barcode sequence comprising a third barcode and a fourth barcode having a sequencing adapter disposed therebetween, said sequencing adapter comprising a third primer site and a fourth primer site having a linker disposed therebetween. In some embodiments, the first primer site of the sense strand of the template nucleic acid and the third primer site of the antisense sense strand of the template nucleic acid comprise the same sequence. Some embodiments also include a step (c) selecting for template nucleic acids comprising transposon sequences wherein the first transposon sequence is non-contiguous with the second transposon sequence and transposon sequences comprising a linker. In some embodiments, the linker comprises an affinity tag adapted to bind with a capture probe. In some embodiments, the affinity tag is selected from the group consisting of His, biotin, and streptavidin. In some embodiments, each barcode is different. In some embodiments, the linker comprises a single-stranded nucleic acid. In some embodiments, the target nucleic acid comprises genomic DNA.

Methods for Obtaining Haplotype Information

Some embodiments of the methods and compositions provided herein include methods of obtaining haplotype information from a target nucleic acid. Haplotype information can include determining the presence or absence of different sequences at specified loci in a target nucleic acid, such as a genome. For example, sequence information can be obtained for maternal and paternal copies of an allele. In a polyploidy organism, sequence information can be obtained for at least one haplotype, Such methods are also useful in reducing the error rate in obtaining sequence information from target nucleic acid.

Generally, methods to obtain haplotype information include distributing a nucleic acid into one or more compartments such that each compartment comprises an amount of nucleic acid equivalent to about a haploid equivalent of the nucleic acid, or equivalent to less than about a haploid equivalent of the nucleic acid. Sequence information can then be obtained from each compartment, thereby obtaining haplotype information. Distributing the template nucleic acid into a plurality of vessels increases the probability that a single vessel includes a single copy of an allele or SNP, or that consensus sequence information obtained from a single vessel reflects the sequence information of an allele or SNP. As will be understood, in some such embodiments, a template nucleic acid may be diluted prior to compartmentalizing the template nucleic acid into a plurality of vessels. For example, each vessel can contain an amount of target nucleic acids equal to about a haploid equivalent of the target nucleic acid. In some embodiments, a vessel can include less than about one haploid equivalent of a target nucleic acid.

Method of Haplotyping with Virtual Compartments

Some methods of obtaining haplotype information provided herein include the use of virtual compartments. Advantageously, some such methods enable compartments to include amounts of nucleic acids equivalent to at least one or more haploid equivalents. In other words, such methods enable the use of higher concentrations of nucleic acids in compartments compared to other methods of haplotyping, thereby increasing the efficiency and yields of various manipulations.

In some methods to obtain haplotype information with virtual compartments, a nucleic acid is compartmentalized into a plurality of first vessels, and the nucleic acids of each compartment are provided with a first index; the first-indexed nucleic acids are combined, and then compartmentalized into a plurality of second vessels, and the nucleic acids of each compartment are provided with a second index. A template nucleic acid can be prepared by undergoing at least 2, 3, 4, 5, 6, 7, 8, 9, 10 or more rounds of compartmentalizing, indexing, and pooling. In such a manner, a template nucleic acid is provided with a plurality of different indices in a stepwise method. Subsequent to indexing, the indexed template nucleic acids can be pooled and distributed into a plurality of compartments such that each compartment is likely to include an amount of a particular template nucleic acid having a particular combination of indexes that is equivalent to about a haploid equivalent of the target nucleic acid, or equivalent to less than about a haploid equivalent of the target nucleic acid, or equivalent to more than about a haploid equivalent. In other words, each vessel can receive an amount of template nucleic acid comprising more than the equivalent of a haploid equivalent, however, each copy of an allele or SNP is likely to be associated with a different combination of indexes. Accordingly, the number of vessels to compartmentalize a template nucleic acid such that each vessel includes about an amount of template nucleic acid equivalent to a haploid or less of a target nucleic acid can be reduced. In addition, the amount of nucleic acid in each vessel can be greater than the amount of about a haploid equivalent, thereby increasing the efficiency and yields of various manipulations.

There are various methods to index nucleic acids. For example, in some embodiments, indexes may be inserted into nucleic acids using transposomes provide herein; indexes can be ligated to nucleic acids; and indexes can be added to nucleic, acids during copying, e.g., amplification of a nucleic acid. In some embodiments, a template nucleic acid comprising an index can be prepared using transposomes comprising a contiguous transposon sequence. See e.g., transposome (50) in FIG. 1. Insertion of contiguous transposon sequences can result in the preservation of positional information for a particular nucleic acid molecule after distribution of template nucleic acids between several compartments. In some embodiments, a template nucleic acid comprising an index can be prepared using transposomes comprising non-contiguous transposon sequences. See e.g., transposome (10) in FIG. 1. Examples of such transposon sequences are set forth in U.S. Patent Application Publication No. 2010/0120098, which is incorporated herein by reference in its entirety. Insertion of non-contiguous transposon sequences can result in the fragmentation of a particular nucleic acid molecule. Thus, in some embodiments, insertion of non-contiguous transposon sequences into a template nucleic acid can reduce positional information for a particular nucleic acid molecule after distribution of the template nucleic acids between several compartments. In other words, different fragments of a particular nucleic acid molecule can be distributed into different vessels.

Figure 4:
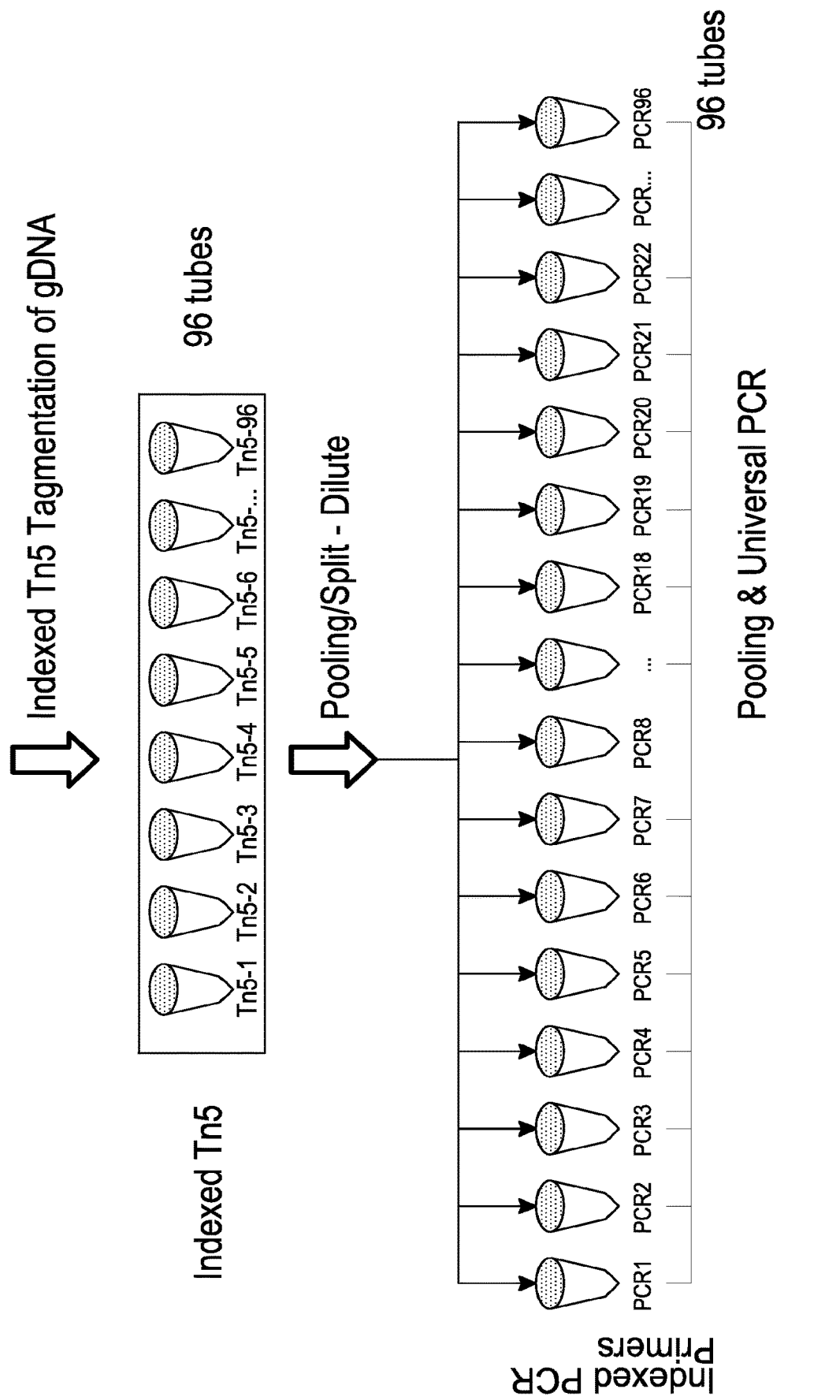
FIG. 4 depicts a scheme for preparing template nucleic acids to obtain sequence information in which a target nucleic acid is compartmentalized into 96 tubes, indexed by insertion of Tn5 derived transposons, indexed nucleic acids are combined, and further compartmentalized into 96 tubes, further indexed by amplification, the twice indexed nucleic acids may then be combined.

In an example with a diploid genome, after pooling and dilution in compartments, a greater amount of nucleic acids can be added to each compartment since the chance of a copy from the father and copy from the mother of the same region with the same indexes is lower. For example, one copy of the father and one copy of the mother for the same region can be present in the same compartment as long as each contains a different index, for example, one comes from a transposition reaction with a first index (index-1) and the other comes from a transposition reaction with a different first index (index-2). In other words, copies of the same region/chromosome can be present in the same compartment since these can be distinguished by their unique index incorporated in the first transposition reaction. This allows more DNA to be distributed into each compartment compared to alternative dilution methods. The dual indexing scheme creates a total number of virtual compartments of number of initial indexed transposition reactions multiplied by the number of indexed PCR reactions, FIG. 4 depicts an example embodiment of obtaining haplotype information using virtual compartments. A target nucleic acid comprising genomic DNA is distributed into a first set of 96 vessels and the nucleic acids of each vessel are provided with a different first index using a Tn5-derived transposon. Thus a plurality of first-indexed template nucleic acids is obtained (e.g., Tn5-1, Tn5-2 . . . and Tn5-96). The plurality of first-indexed template nucleic acids are combined and then redistributed into a second set of 96 vessels and the nucleic acids of each vessel are provided with a different second index by amplification of the nucleic acids using primers comprising the second indexes. Thus a plurality of second-indexed template nucleic acids is obtained (e.g., PCR1, PCR2 . . . , and PCR96). The plurality of second-indexed template nucleic acids can be combined and sequence information obtained. The use of 96×96 physical vessels is equivalent to 9216 virtual compartments.

Methods to Obtain Extended Haplotype Information

As described above, insertion of non-contiguous transposon sequences into the template nucleic acid can reduce positional information for a particular nucleic acid molecule, for example, after distribution of the template nucleic acids between several compartments. However, applicant has discovered methods to preserve such positional information for a particular nucleic acid molecule. Without being bound to any one theory, it has been observed that after transposition, the resulting two adjacent fragments of a particular nucleic acid molecule will tend to be distributed into the same vessel under conditions that maintain the transposase at the site of insertion of a transposon sequence. In other words, the transposase may hold the two resulting two adjacent fragments of a particular nucleic acid molecule together.

In some embodiments, a transposase can be removed from a template nucleic acid subsequent to distributing the template nucleic in several vessels. A transposase can be removed from the site of an insertion by various methods well known in the art, including the addition of a detergent, such as SDS, changing temperature, Proteinase digestion, chaperone capture and changing pH. DNA polymerases, with or without strand displacement properties including, but not limited to, phi29 DNA polymerase, Bst DNA polymerase, etc. can also be used to dislodge the transposase from the DNA.

Figure 5:
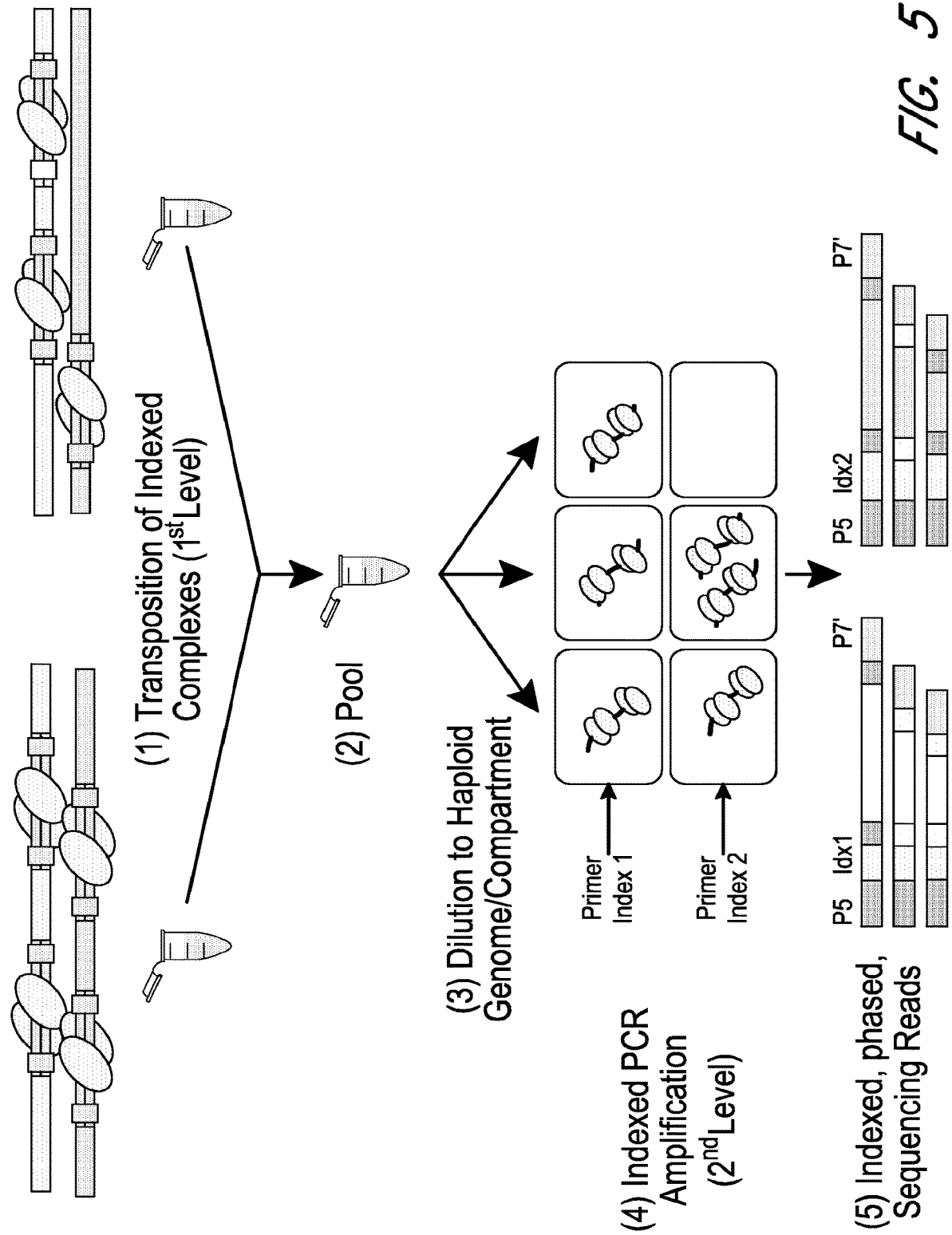
FIG. 5 depicts a schematic embodiment for obtaining haplotype sequence information in which a template nucleic acid is indexed with the barcode of a transposon, and with a primer. A template nucleic acid is prepared by insertion of a looped transposon into a target nucleic acid. The template nucleic acid is diluted into compartments. The template nucleic acid of each compartment is indexed by amplification with a primer. Indexed template nucleic acids are sequenced, aligned, and sequence representation is obtained.

FIG. 5 depicts an example scheme in which a target nucleic acid is distributed into a set of first vessels and indexed by insertion of transposomes, such as transposomes comprising non-contiguous transposon sequences. The first indexed template nucleic acids are pooled and distributed into a set of second vessels and indexed by PCR amplification. Sequence information can be obtained from the second indexed template nucleic acids.

Some methods of obtaining extended haplotype information from a target nucleic acid include (a) obtaining a template nucleic acid comprising a plurality of transposomes inserted into the target nucleic acid, wherein at least some of the inserted transposome each comprise a first transposon sequence, a second transposon sequence noncontiguous with the first transposon sequence, and a transposase associated with the first transposon sequence and the second transposon sequence; (b) compartmentalizing the template nucleic acid comprising the plurality of inserted transposomes into each vessel of a plurality of vessels; (c) removing the transposase from the template nucleic acid; and (d) obtaining sequence information from the template nucleic acid of each vessel, thereby obtaining haplotype information from the target nucleic acid. In some embodiments, compartmentalizing the template nucleic acid includes providing each vessel with an amount of template nucleic acid equivalent to greater than about a haploid equivalent of the target nucleic acid, an amount of template nucleic acid equivalent to about one haploid equivalent of the target nucleic acid, or an amount of template nucleic acid equivalent to less than about a haploid equivalent of the target nucleic acid.

An additional embodiment for maintaining contiguity of target nucleic acids for sequencing applications comprises utilizing one-sided (i.e., one transposon end) transpositional events in lieu of two-sided (i.e., two transposon ends) transpositional events as disclosed herein. For example, transposases including, but not limited to Mu, MuE392Q mutant, Tn5 have been shown to display one-sided transposition of a transposon sequence into a target nucleic acid (Haapa et al., 1999, Nucl. Acids Res, 27(3): 2777-2784). The one-sided transpositional mechanism of these transposases can be utilized in methods described here to maintain the contiguity of a sample for sequencing, for example to haplotype or assemble a target nucleic acid.

In one example of one-sided transposition into a target DNA the transposome, a Tn5 dimer transposase is associated with only one transposon sequence end. In preferred embodiments, the transposon end could further comprise additional sequences such as index sequences, barcodes, and/or primer sequences and the like which could be used, for example, to identify a sample, amplify or extend the target nucleic acid and align fragment sequences. The transposome complex associates with the target nucleic acid, in that case dsDNA. At the site of transposome association, the transposase cleaves that strand of the target DNA and inserts the transposon and any other additional sequences at the point of cleavage. The transposase remains associated with the target DNA until it is removes, for example after partitioning of the sample as described herein the transposase can be removed by degradation (e.g., use of SDS or other methods as described here). The target nucleic acid, in this case dsDNA, does not fragment after removal of the transposase, as such the transposon and any additional sequences can be incorporated into the target DNA without fragmenting the DNA. Once the transposase is removed, target amplification by any means known in the art, in this example single or multiple primer amplification (due to incorporation of multiple different primer sequencing included in one or more transposons) either exponential or linear such as targeted PCR or whole genome amplification (for example by multiple strand displacement), can be performed to create libraries for sequencing. As described herein with respect to the two-sided transposon sequences, a variety of different combinations of index, barcode, restriction endonuclease site(s), and/or primer sequence could be included as part of the transposon sequence depending on the needs of the user. As such, one-sided transposome complexes could also be utilized to maintain contiguity of a target nucleic acid for methods disclosed herein for determining the haplotype of a target nucleic acid.

One sided transposomes can also be created from the two transposon/transposase complexes or the looped transposon/transposase complexes disclosed herein. For example, one of the transposon sequences of a two transposon complex or one end of the lopped transposon could be, for example, chemically modified or blocked so that transposition would not occur, or would minimally occur, at that end. For example, a dideoxynucleotide, a hapten such as a biotin could be incorporated at the end of one of the transposon ends which would inhibit transposition at that end, thereby allowing for only one transposon, or one end of a looped transposon, to be inserted into the target nucleic acid.

In one embodiment, a method of obtaining sequence information from a target nucleic acid comprises obtaining a template nucleic acid comprising a plurality of transposons inserted into said target nucleic acid such that the contiguity of the template is retained, compartmentalizing the nucleic acids comprising the plurality of inserted transposons into a plurality of vessels, generating compartment-specific indexed libraries from the transposed nucleic acid targets and obtaining sequence information from the template nucleic acids in each vessel of the plurality of vessels.

Certain Methods for Preparing Target Nucleic Acids for Haplotyping

Some embodiments of the methods and compositions provided herein include preparing target nucleic acids for haplotyping using the methods provided herein. Using a pre-amplification method, the number of unique reads is increased by generating multiple identical copies of the same nucleic acid fragment as a contiguous product. In some such embodiments, a library is amplified by methods such as rolling circle amplification (RCA). In some embodiments, circular libraries of a target nucleic acid are prepared and the library amplified by RCA. Such methods generate extended long nucleic acids.

Figure 6:
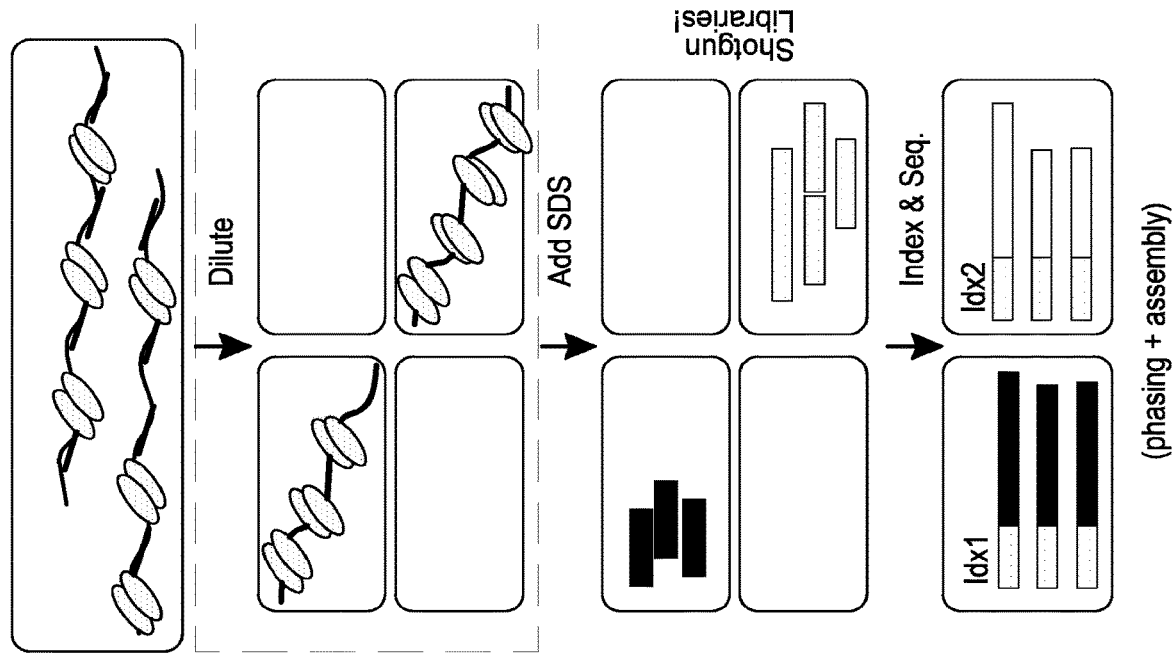
FIG. 6 depicts a scheme that includes preparing a target nucleic acid using matepair and rolling circle amplification, followed by insertion of transposomes into the target nucleic acid, dilution of the target nucleic acid to obtain haplotype information, removal of the transposase by addition of SDS, generation of shotgun libraries, indexing and sequencing.
Figure 6:
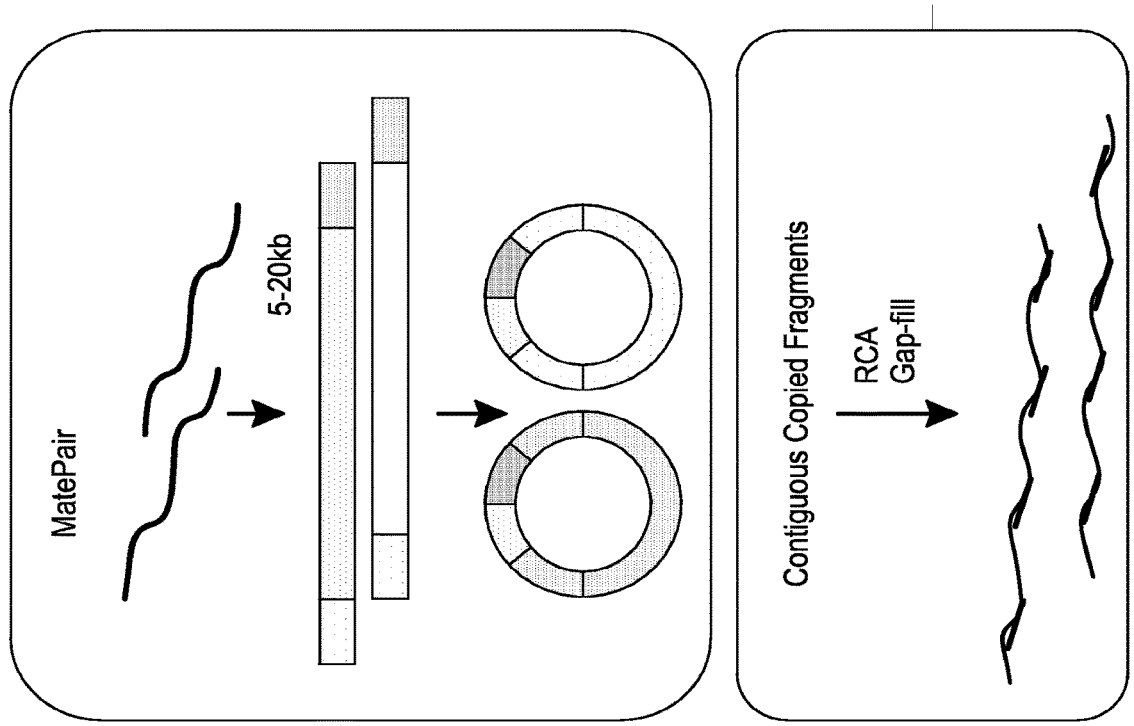

An example scheme is shown in FIG. 6. FIG. 6 depicts a method including preparing target nucleic acids for haplotyping by generating a library comprising circular molecules by mate-pair and selection of specific or range of sizes from 1-10 kb or 10-20 kb, or 20 kb-50 kb, 50-200 kb nucleic acids; amplifying the library by RCA to generate extended lone nucleic acids; inserting indexes into the amplified library with transposons; compartmentalizing the inserted library; removing transposase with SDS; further indexing the library; and obtaining sequence information from the library.

Figure 7:
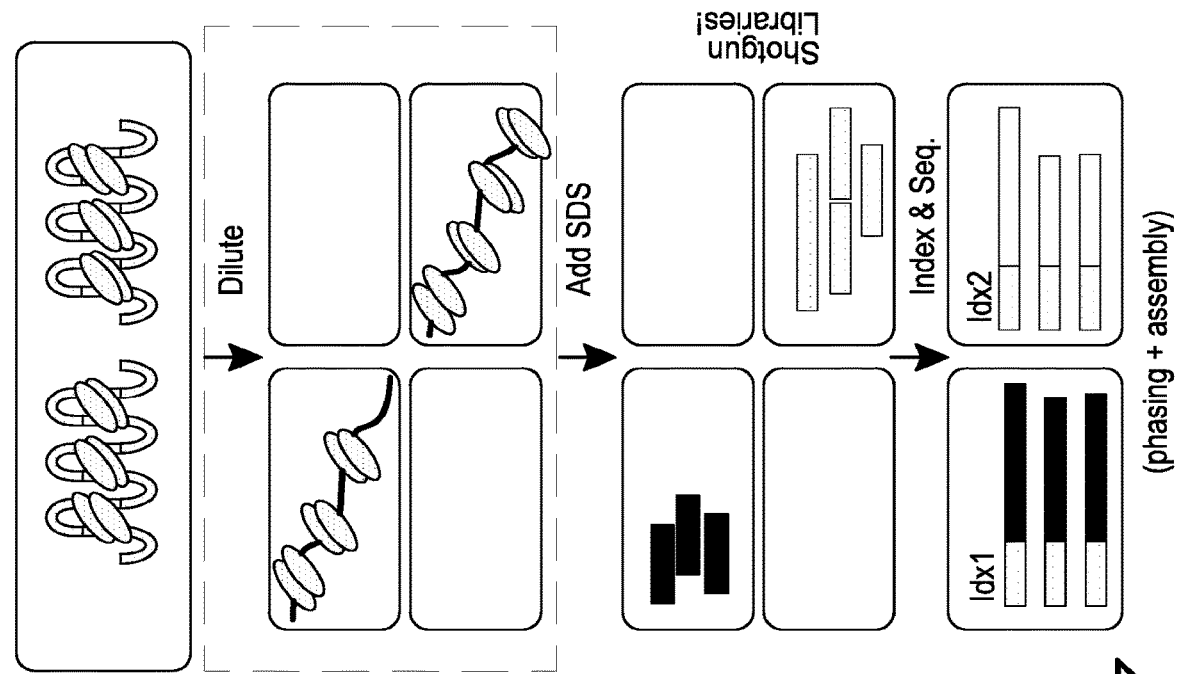
FIG. 7 depicts a scheme that includes preparing a target nucleic acid using hairpin transposition and rolling circle amplification, followed by insertion of transposomes into the target nucleic acid, dilution of the target nucleic acid, removal of the transposase by addition of SDS, generation of shotgun libraries, indexing and sequencing to obtain haplotype information.
Figure 7:
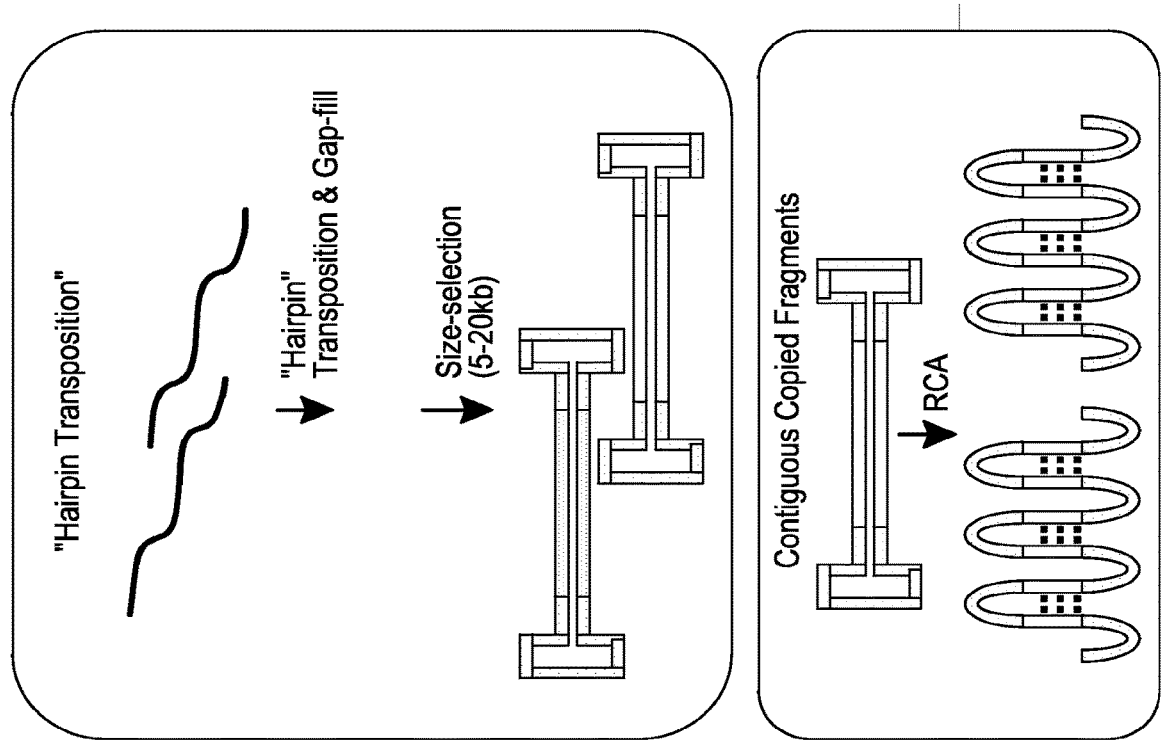

Another example scheme is shown in FIG. 7. FIG. 7 depicts a method including preparing target nucleic acids for haplotyping by generating a library comprising circular molecules by hairpin transposition, gap fill, and selection of a specific size or range of sizes from 1-10 kb or 10-20 kb, or 20 kb-50 kb, 50-200 kb5nucleic acids; amplifying the library by RCA to generate extended lone nucleic acids; inserting indexes into the amplified library with transposons; compartmentalizing the inserted library; removing transposase with SDS; further indexing the library; and obtaining sequence information from the library.

Methods to Generate Mate-Paired Libraries

Methods for generating mate-pair libraries include; fragmenting genomic DNA into large fragments typically greater than (though not limited to) 1000 bp; circularizing individual fragments by a method that tags the ligated junction; fragmenting the DNA further; enriching the tagged junction sequences and ligating adaptors to the enriched junction sequences so that they may be sequenced yielding information about the pair of sequences at the ends of the original long fragment of DNA. These processes involve at least 2 steps where DNA is fragmented, either physically or enzymatically. In at least one or more distinct steps, adaptors are ligated to the ends of fragments. Mate-pair preps typically take 2-3 days to perform and comprise multiple steps of DNA manipulations. The diversity of the resulting library correlates directly with the number of steps required to make the library.

The method provided herein simplifies the number of steps in the library generation protocol by employing a transposase mediated reaction that simultaneously fragments and adds adaptor sequences to the ends of the fragments. At least one or both of the fragmentation steps (initial fragmentation of genomic DNA and fragmentation of circularized fragments) may be performed with a transposome, thus replacing the need for separate fragmentation and adaptor ligation step. Obviating the polishing, preparation of, and ligation to fragment ends reduces the number of process steps and thus increases the yield of usable data in the prep as well as making the procedure more robust. In one embodiment, the protocol can be performed without resorting to methods that purify a selection of sizes based on electrophoresis. This method produces a broader range of fragment sizes than can be achieved with gel electrophoretic, methods but nonetheless produces usable data. The advantage is that a labour intensive step is avoided.

Figure 8:
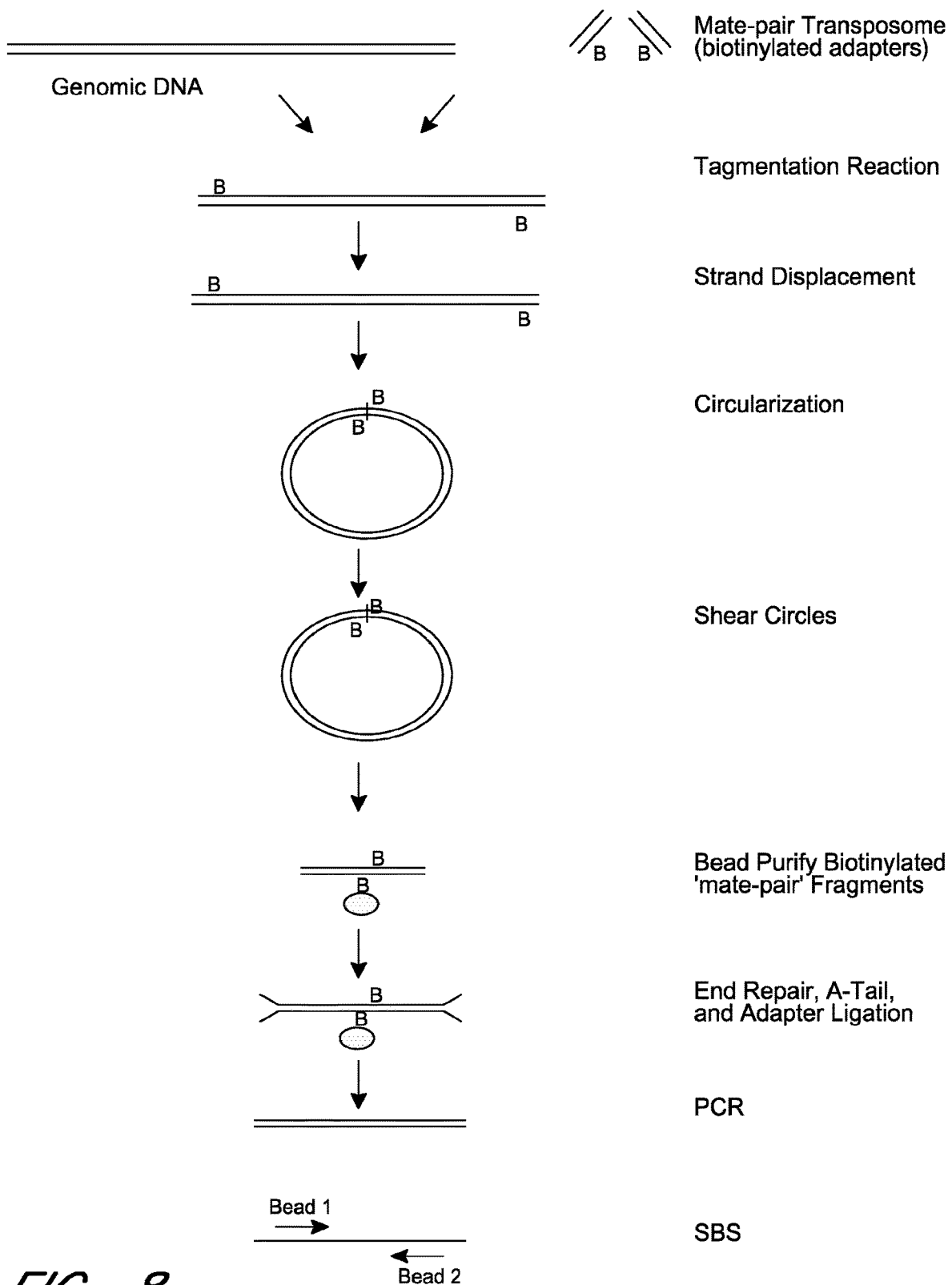
FIG. 8 depicts an example scheme for generation of mate pair libraries.
Figure 9:
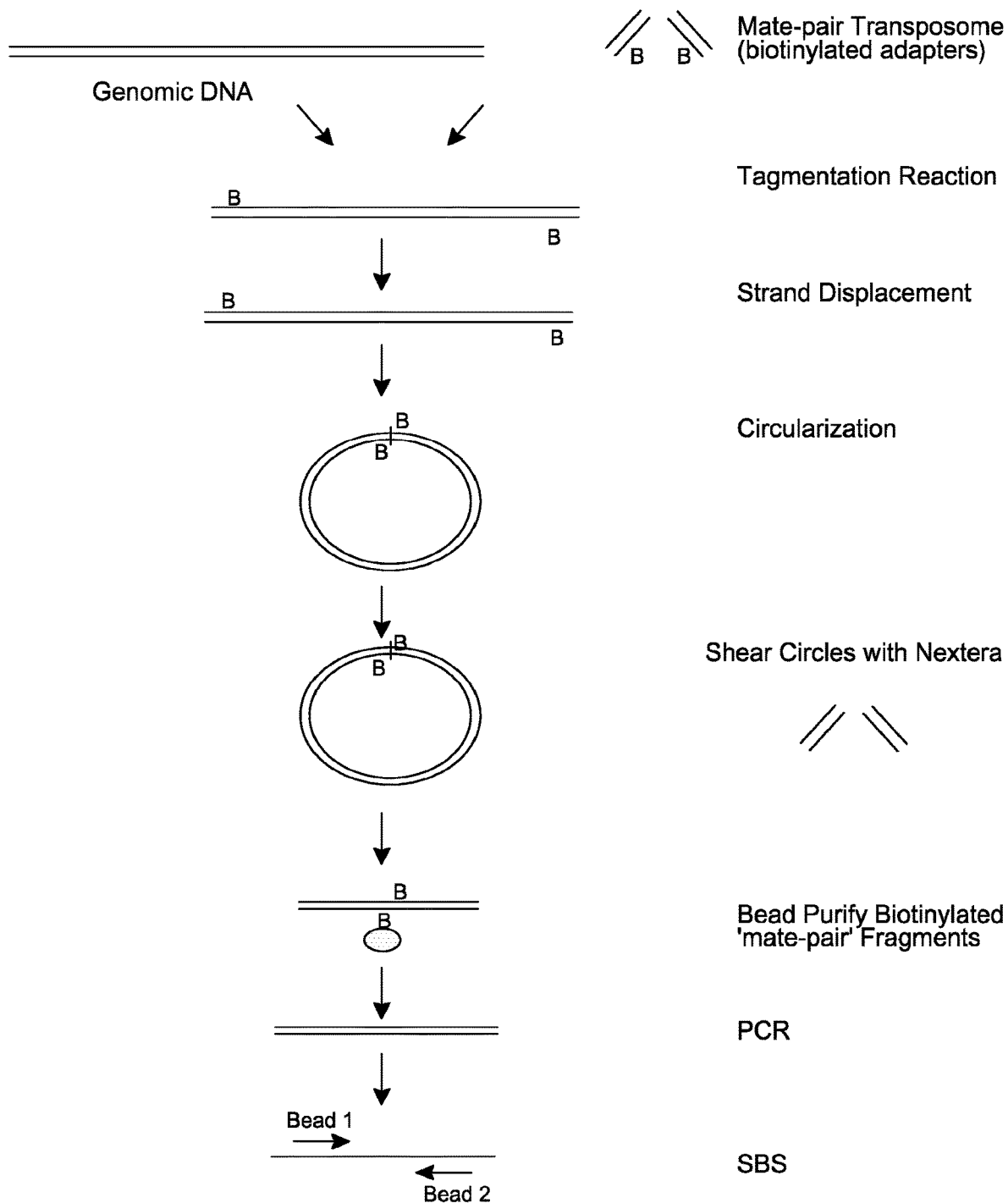
FIG. 9 depicts an example scheme for generation of mate pair libraries.

FIG. 8 provides an example scheme where just the initial fragmentation is replaced with a transposome tagmentation step. The circularized DNA is fragmented by either physical methods or chemical/enzymatic methods and the fragments turned into a library via application of standard sample prep protocols (e.g. TRUSEQ). FIG. 9 illustrates an example scheme where both the initial fragmentation and the circularized DNA fragmentation are performed with a transposome tagmentation step. The adaptor sequences for the transposome (including the ME sequences) may or may not be different for the adaptor used for the initial tag mentation and the subsequent circle tagmentation.

Amplifying template nucleic acid by generating multiple copies of each molecule before transposition or introduction of molecular indexes creates redundancy which can be useful for getting higher SNP coverage in each haplotype block, and also for de novo genome assembly, similar to a shotgun approach. Template nucleic acid can be converted to a defined-size library by low-frequency transposition, physical shearing, or enzymatic digestion, and then amplified for a finite number of cycles by either PCR or a whole genome amplification scheme (for example using phi29). The amplified library which already contains the built-in redundancy can be used as the input material for the haplotyping workflow. This way, every region of the genome is represented multiple times by multiple copies generated upfront with each copy contributing a partial coverage of that region; however, the consensus coverage will be closer to complete.

EXAMPLES

Example 1—Reducing Error Rates

Figure 10:
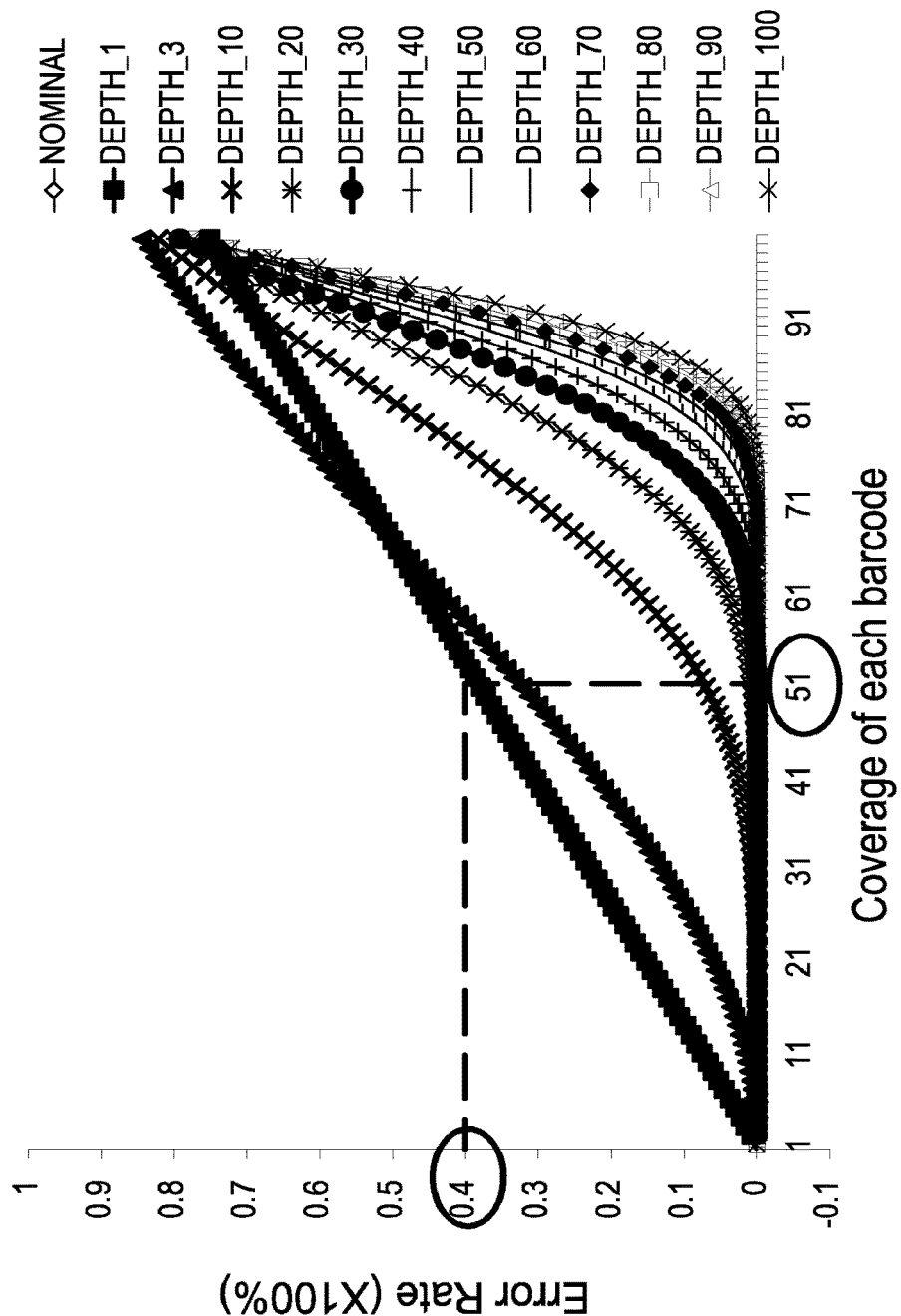
FIG. 10 is a graph depicting a model of error rate in sequence information for the number of times a particular sequence associated with a barcode is sequenced.

A library of template nucleic acids was prepared with each fragment comprising a different barcode. Each fragment was amplified and sequence information was obtained from at least one amplified product from each fragment. A consensus sequence was determined from the sequence information from the amplified products from each fragment. In particular, a NEXTERA-prepped sequencing library was sequenced for 500 cycles on a MISEQ instrument. The library consisted of a distribution of sizes, with maximum read lengths extending to ~300 nt. The error rates at cycle 250 were approximately 15%, If a template was represented just three times, the error rate dropped to ~1% at cycle 250. FIG. 10 illustrates a model of error rates with number of amplified products sequenced (coverage of each barcode). Error rates decrease as the number of amplified products sequenced from a fragment increase.

Example 2—Coupling Transposon Sequences

This example illustrates methods to couple two transposon sequences together in various orientations including a 5'-5' orientation, and a 3'-3' orientation. In an exemplary method, aldehyde oxyamine is used to form linked oligos via oxime ether formation. An aldehyde modified oligo (either on the 5' or the 3' end) is combined with an oligo modified with an oxyamine on the 5' end in reaction buffer and allowed to incubate for 2 hours. Final product can be isolated via PAGE purification for example.

Figure 11:
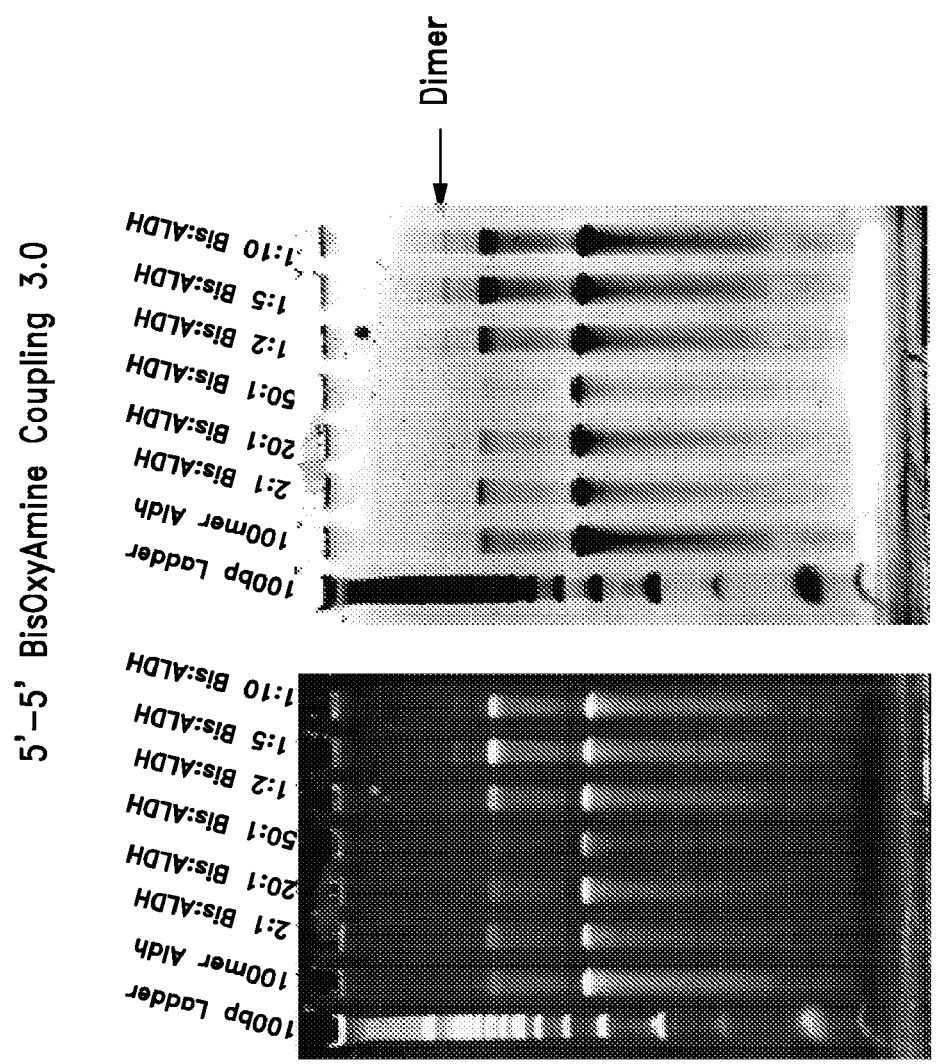
FIG. 11 depicts images of agarose gels showing oligonucleotides linked with 5'-5' bisoxyamine coupling, in which looped precursor transposons are indicated by the dimer band.

In another exemplary method, bisoxyamine coupling was performed, Aldehyde modified oligos were dimerized with a bis-oxyamine (e.g., dioxyamino butane) linker using locally high concentrations to force hi-substitution. 100-mer oligos were synthesized with an aldehyde on the 5' end and purified. The bisoxyamine oligo was synthesized. A 1 mM solution of the bisoxyamine oligo was made in a low pH reaction buffer containing a catalyst (5 M urea, 100 mM aniline, 10 mM citrate, 150 mM NaCl, pH 5.6) and added to a 665 µM solution of aldehyde oligo in water. The entire volume of the solution was diluted 1:1 with reaction buffer, and allowed to incubate at room temperature for 2 hours. A titration of various aldehyde: bisoxyamine ratios showed dimerization at high bisoxyamine ratios. The most successful conditions were replicated with 3' aldehyde oligos. FIG. 11 shows results of 5'-5' bisoxyamine coupling reactions in which looped precursor transposons were observed in the indicated dimer band. Similar results were observed for 3'-3' bisoxyamine coupling reactions.

Example 3—Monitoring Transposome Stability

Transposomes were prepared using long and short transposon sequences loaded onto transposase. The transposome products included: A (2 short sequences); B (long and short sequences); and C (2 long sequences). The relative amounts of each species of transposome were measured under various conditions, such as temperature, buffers, ratios of transposon sequences to transposase. Generally, high NaCl or KCl salt increased exchange of transposon sequences between transposomes. Glutamate and acetate buffers eliminated or reduced exchange, with preferred concentrations between 100-600 mM, Optimum storage conditions were determined.

Example 4—Maintaining Template Contiguity

Figure 12:
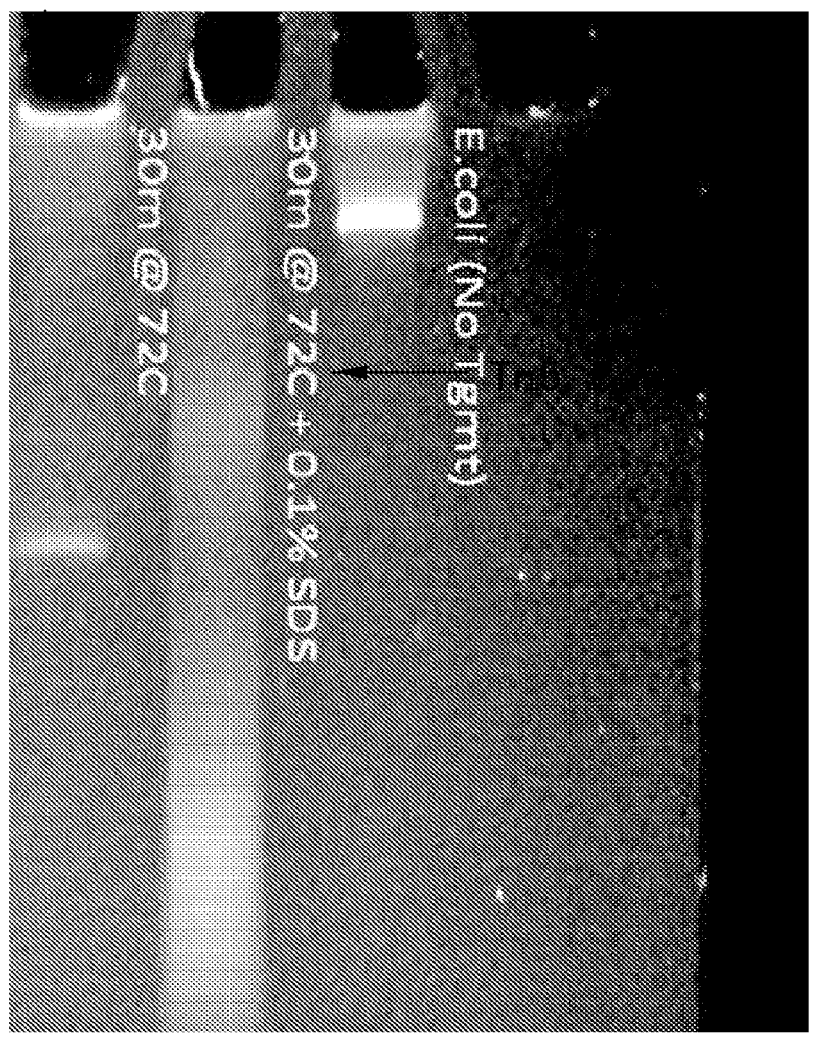
FIG. 12 is an image of an agarose gel showing the apparent molecular weight of a transposed target nucleic acid associated with transposase (left lane), and without transposase (+0.1% SDS, middle lane).

This example illustrates a method for maintaining contiguity information of a template nucleic acid prepared using transposomes comprising non-contiguous transposon sequences in which Tn5 transposase stays bound to the template DNA post-transposition. Target nucleic acid was contacted with transposomes comprising Tn5 transposase, and non-contiguous transposon sequences. FIG. 12 shows that samples further treated with SDS appeared as a smear of various fragments of template nucleic acid; samples not treated with SDS showed retention of putative high molecular weight template nucleic acid. Thus, even though a nucleic acid may be fragmented, adjacent sequences may still be associated with one another by the transposase (as demonstrated by the Tn5 bound DNA left in the wells).

Figure 13:
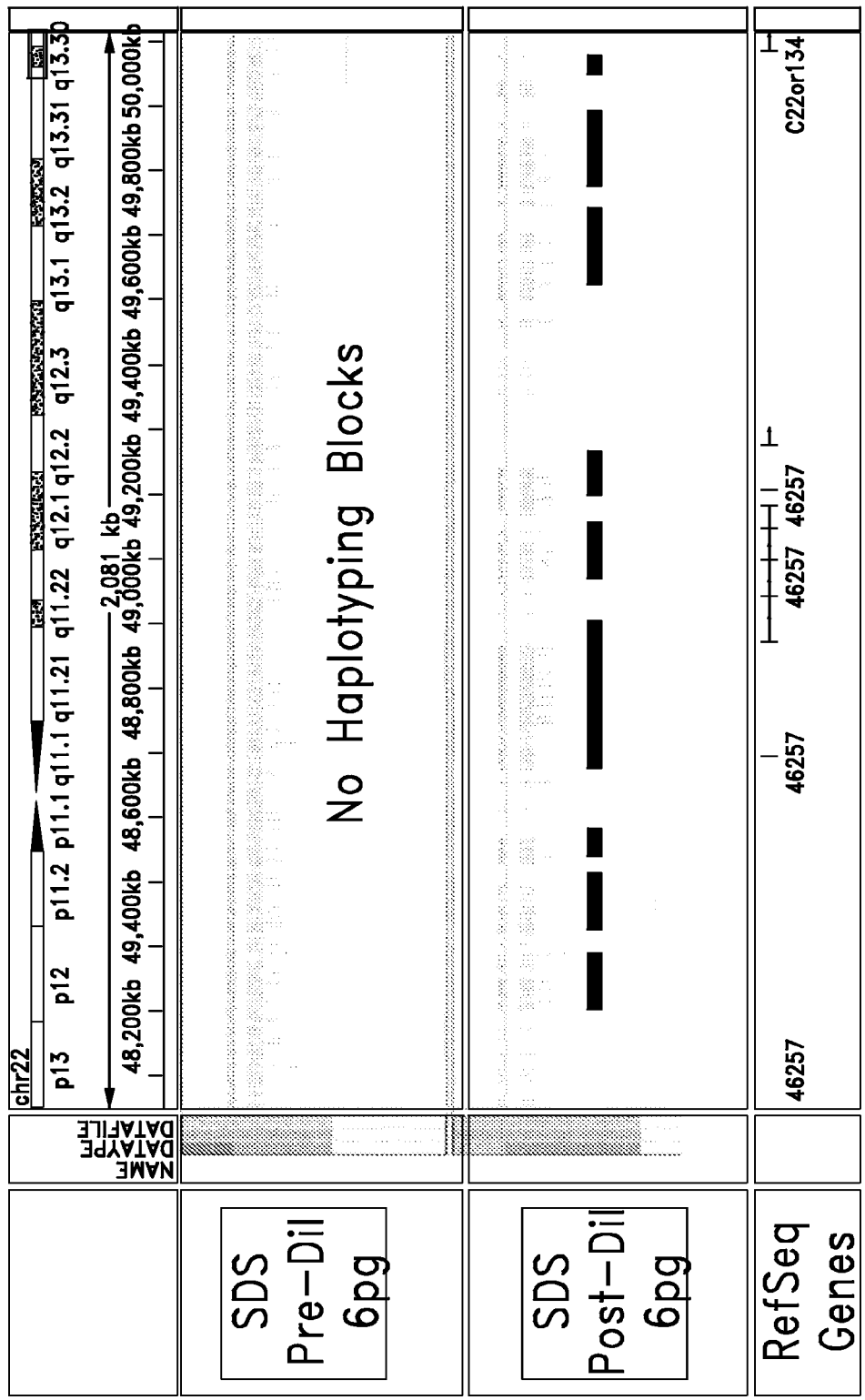
FIG. 13 summarizes that haplotype blocks up to 100 kb were observed for samples in which transposase was removed by SDS post-dilution.

In still another exemplary method, a library of template nucleic acids was prepared using transposomes comprising non-contiguous transposon sequences with target nucleic acid comprising human Chromosome 22. FIG. 13 summarizes that haplotype blocks up to 100 kb were observed for samples in which transposase was removed by SDS postdilution. Thus, by practicing methods as described herein target nucleic acids can maintain target integrity when transposed, be diluted, and be transformed into sequencing libraries.

Example 5—Maintaining Template Contiguity

Target nucleic acids were tagmented with transposomes comprising non-contiguous transposon sequences (NEXTERA), diluted to the desired concentration, and then treated with SDS to remove the transposase enzyme before PCR. As a control, the same amount of input DNA was tagmented, treated with SDS first and then diluted to the desired concentration, SDS treatment before dilution removes proximity information since the transposase enzyme dissociates from the target DNA with SDS, thereby fragmenting the target DNA. Two tagmentation reactions were set-up on 50 ng of a Coriell gDNA, 1 reaction was stopped with 0.1% SDS and diluted to 6 μg. Next, the other reaction was first diluted to 6 pg and then stopped with 0.1% SDS. The entire reactions were used to set up a 30-cycle PCR reaction and sequenced on a Gene Analyzer platform (Illumina), according to the manufacturer's instructions. The reads were mapped to a human reference genome and the distance distribution was calculated and plotted.

Figure 14:
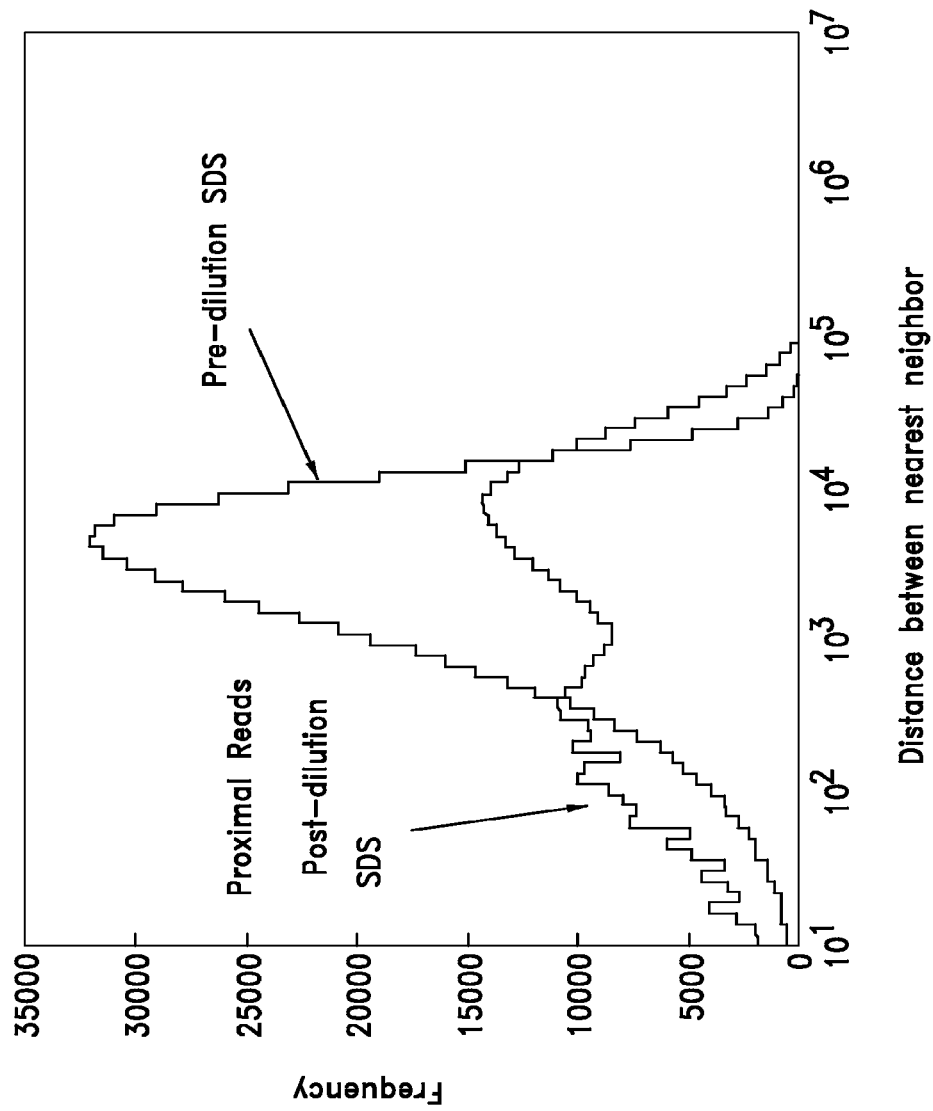
FIG. 14 depicts a graph showing the frequencies of sequencing reads for particular distances between neighboring aligned reads for template nucleic acids prepared by adding SDS to remove transposase before dilution to obtain haplotype information, or after dilution to obtain haplotype information.

As shown in FIG. 14, in the SDS-PostDilution sample, the median distance shifted to smaller sizes and a large subpopulation of proximally located reads becomes apparent. If there was any haplotyping, pile up of proximal reads was expected. The bi-modal distribution of post-dilution sample demonstrated that there is an enrichment of proximal reads.

Figure 15:
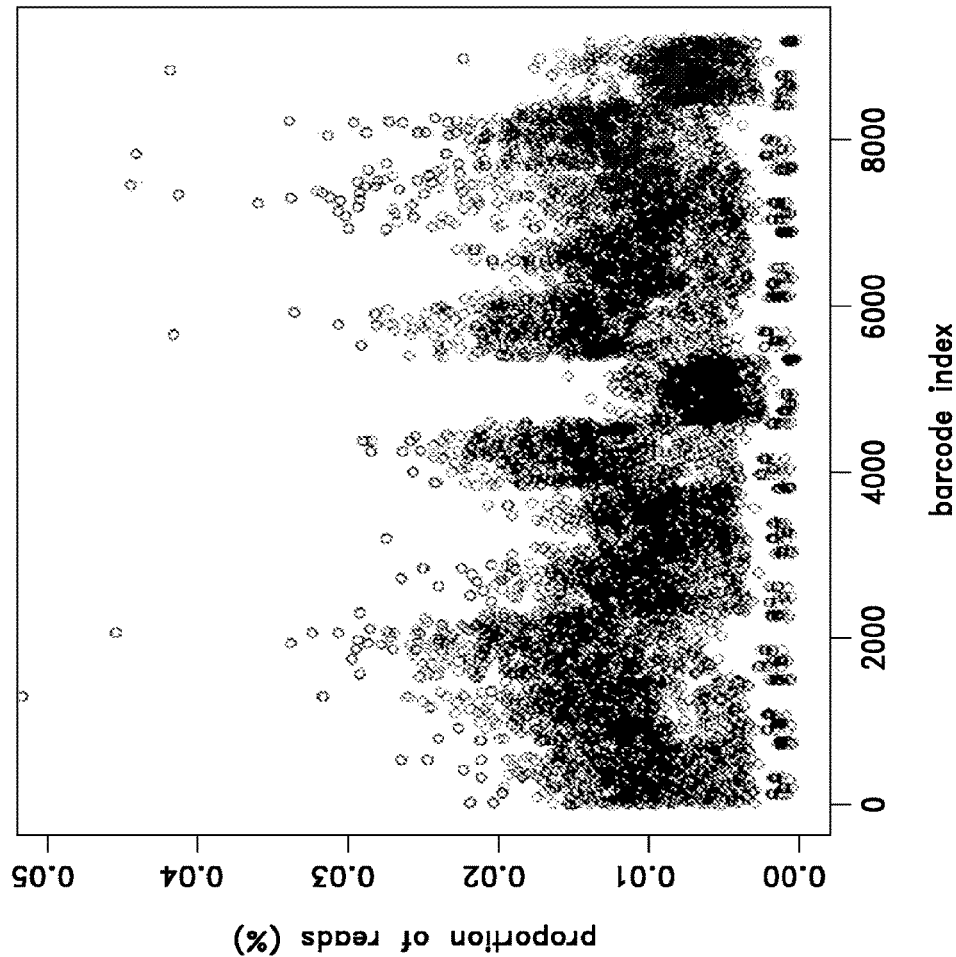
FIG. 15 shows a graph of barcode indices and proportion of reads and demonstrates that all 9216 different compartments in a 96×96 indexing scheme were observed.

The distance distribution was a measure of sample size (i.e. the more unique reads, the shorter the distance). The distance histogram for SDS-PreDilution and SDS-PostDilution samples are shown in FIG. 14. To correct for the difference in the number of unique reads, the Pre-Dilution was down-sampled to give the same number of unique mapped reads (664,741). A significant enrichment was observed for reads that are immediate neighbors (i.e. junctions). This was measured by looking at the "distance to next alignment' distribution and finding the reads which their distance to their next alignment is the sequence read length minus 9 (which correspond to 9 bp duplication caused by Tn5 at the insertion site). Such reads make up 10% of the data (FIG. 15) and with employment of single primer system for amplification of NEXTERA libraries, can be doubled. Also implementation of a more conservative sample prep which allows less sample loss allows recovery of more junction data. The haplotype resolving power diminished when input DNA was increased. On the other hand, reducing the DNA input required more amplification, and therefore more PCR cycles, generating many PCR duplicates. Using individually barcoded Tn5 complexes allowed the tagmentation and subsequent dilutions to be carried out in separate compartments. Low levels of input from individually barcoded and tagmented material were combined to elevate the PCR input DNA amounts to the level that allowed more specific amplification with less waste of sequencing capacity on redundant reads. Accordingly, using sufficient barcoded complexes allowed phasing of the majority of the human genome. In order to increase the haplotype resolving power, barcoding was implemented at both the complex level and PCR primer level. Such combinatorial indexing scheme allows the use of very low input DNA from each individually barcoded complex into PCR reaction, which would allow powerful haplotype resolution. Using only 40 indexing oligos (8+12=20 for NEXTERA complexes which generates 8*12=96 individual complexes and 8+12=20 for PCR primers which would allow 8*12=96 additional indexes), 96*96=9216 virtual compartments were generated for the abovementioned haplotyping workflow. Using a modified sequencing recipe, all the data was sequenced on a HiSeq-2000. All 9216 possible barcode combinations were observed in the sequencing results.

Example 6—Obtaining Haplotype Information with Mu

Figure 16:
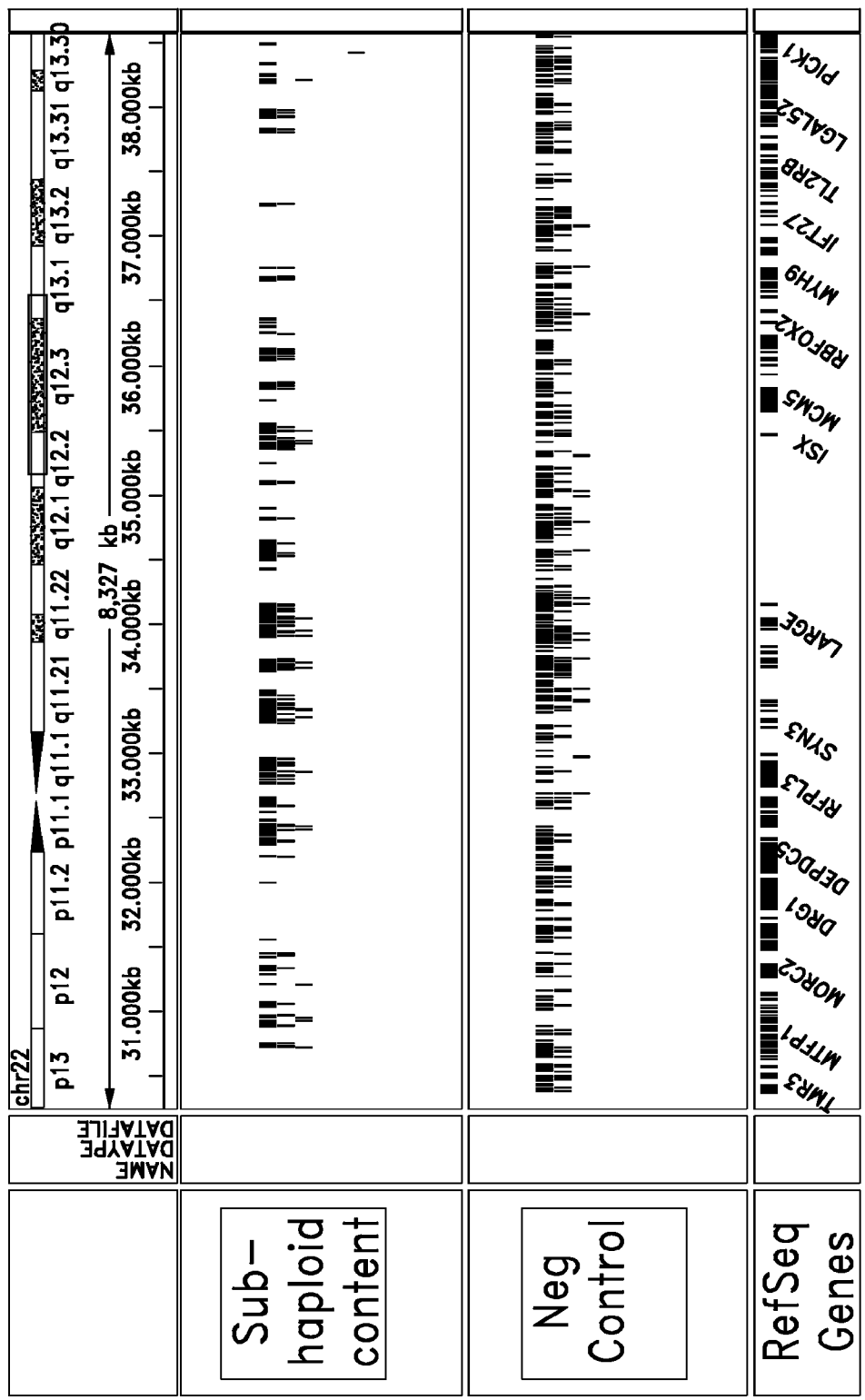
FIG. 16 depicts a Pile up analysis of haplotype information obtained using transposomes comprising Mu.

Transposomes comprising Mu were used to obtain haplotype information. 1 ng of genomic DNA was targeted with Mu-TSM in a 50 μl reaction volume with 1×TA buffer and 1, 2, 4, or 8 μl of 25 μM Mu-TSM complexes. Reactions were incubated at 37° C. for 2 hours. Samples were diluted to 1 μg/μl. For Mu inactivation, 10 μl of each sample containing either 1 μg or 5 μg total genomic DNA were prepared. SDS was added to final concentration of 0.05%. Samples were incubated at 55° C. for 20 minutes. The whole sample was used to set-up a 50 μl PCR reaction using NPM. PCR was clone for 30 cycles. PCR samples were cleaned up with 0.6×SPRI and resuspended in 20 μl of re-suspension buffer, Sequencing information was obtained. FIG. 16 shows the observed Pile-up proximal reads observed at sub-haploid content using transposomes comprising Mu.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including hut not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A device for preparing a nucleic acid library, comprising:
    a substrate comprising a plurality of vessels among which a target nucleic acid is distributed, wherein each vessel of the plurality of vessels comprises:
    a portion of the target nucleic acid in an amount less than about one haploid equivalent; and
    a plurality of transposomes comprising an integration enzyme and a nucleic acid comprising a transposase recognition site integrated into the target nucleic acid, each transposome of the plurality of transposomes comprising a first transposon sequence comprising a first index unique to each vessel of the plurality of vessels, and a second transposon sequence, wherein the first transposon sequence and the second transposon sequence are contiguous, wherein the first transposon sequence and the second transposon sequence are in a 5' to 5' orientation and coupled by a single-stranded linker, and wherein the integration enzyme is associated with the first transposon sequence and the second transposon sequence; and
    an integration enzyme removing agent in an amount sufficient to dislodge the integration enzyme from the target nucleic acid.

2. The device of claim 1, wherein the first transposon sequence and the second transposon sequence of at least some of the plurality of transposomes are integrated into the target nucleic acid.

3. The device of claim 1, wherein each transposome of the plurality of transposomes comprises a fragmentation site disposed between the first transposon sequence and the second transposon sequence.

4. The device of claim 1, wherein the first transposon sequence comprises a first primer site and the second transposon sequence comprises a second primer site.

5. The device of claim 4, wherein the first primer site further comprises a first barcode and the second primer site further comprises a second barcode.

6. The device of claim 5, wherein the first barcode and the second barcode are different.

7. The device of claim 1, wherein each vessel of the plurality of vessels further comprises a plurality of tagmented nucleic acids in each vessel, wherein the first transposon sequence and the second transposon sequence of some of the plurality of transposomes are integrated into the plurality of tagmented nucleic acids.

8. The device of claim 7, wherein the substrate comprises a second plurality of vessels into which pooled tagmented nucleic acids from the plurality of vessels are configured to be re-distributed.

9. The device of claim 8, wherein the second plurality of vessels and the plurality of vessels are about equal in number.

10. The device of claim 1, wherein the integration enzyme is a transposase having a first subunit associated with the first transposon sequence and a second subunit associated with the second transposon sequence.

11. The device of claim 1, wherein the integration enzyme removing agent comprises detergent or protease configured to remove the integration enzyme.

12. The device of claim 1, wherein the substrate comprises spheres, microparticles, beads, membranes, slides, plates, micromachined chips, capillary tubes, microwells, microfluidic devices, channels, or filters.

13. A device for preparing a nucleic acid library, comprising:
    pooled tagmented nucleic acids wherein each individual tagmented nucleic acid of the pooled tagmented nucleic acids comprises an integrated transposon sequence comprising a first index, and wherein a first individual tagmented nucleic acid and a second individual tagmented nucleic acid of the pooled tagmented nucleic acids comprise different first indexes that are different from one another such that a plurality of different first indexes are represented in the pooled tagmented nucleic acids;
    a substrate comprising a plurality of vessels among which the pooled tagmented nucleic acids are distributed, wherein each vessel of the plurality of vessels comprises:
    a portion of the pooled tagmented nucleic acids in an amount greater than about a haploid equivalent, wherein each different first index is present in the portion in an amount less than about a haploid equivalent; and
    a plurality of nucleic acids comprising a second index sequence unique to each vessel of the plurality of vessels.

14. The device of claim 13, wherein the plurality of nucleic acids are ligated to primers configured to bind to the pooled tagmented nucleic acids.

15. The device of claim 13, wherein each vessel of the plurality of vessels further comprises dual-indexed nucleic acids comprising the first index and the second index sequence.

16. The device of claim 13, wherein the pooled tagmented nucleic acids comprise a second integrated transposon sequence.

17. The device of claim 13, wherein the plurality of vessels are configured to receive the pooled tagmented nucleic acids from a different plurality of vessels of the substrate.

18. The device of claim 13, wherein the substrate comprises spheres, microparticles, beads, membranes, slides, plates, micromachined chips, capillary tubes, microwells, microfluidic devices, channels, or filters.

19. The device of claim 17, wherein the plurality of vessels are reduced in number relative to the different plurality of vessels.

20. The device of claim 17, wherein the plurality of vessels are equivalent in number relative to the different plurality of vessels.

21. The device of claim 17, wherein the nucleic acid library is prepared from a diploid nucleic acid sample and wherein the pooled tagmented nucleic acids in at least one vessel of the plurality of vessels comprise a nucleic acid region from a maternal chromosome and the same nucleic acid region from a paternal chromosome having different first indexes relative to one another.

22. The device of claim 1, wherein the integration enzyme removing agent comprises one or both of a chaperone, or a polymerase.

23. The device of claim 11, wherein the integration enzyme removing agent comprises SDS detergent.

24. A device for preparing a nucleic acid library, comprising:
   a substrate comprising a plurality of vessels among which a target nucleic acid is distributed, wherein each vessel of the plurality of vessels comprises:
   a portion of the target nucleic acid in an amount less than about one haploid equivalent; and
   a plurality of transposomes comprising an integration enzyme and a nucleic acid comprising a transposase recognition site integrated into the target nucleic acid, each transposome of the plurality of transposomes comprising a first transposon sequence comprising a first index unique to each vessel of the plurality of vessels, a second transposon sequence, wherein the first transposon sequence and the second transposon sequence are contiguous, wherein the first transposon sequence and the second transposon sequence are in a 5' to 5' orientation and coupled by a single-stranded linker, and wherein the integration enzyme is associated with the first transposon sequence and the second transposon sequence; and an integration enzyme removing system coupled to the substrate, wherein the integration enzyme removing system is configured to change a temperature of the substrate an amount sufficient to dislodge the integration enzyme from the target nucleic acid.

* * * * *